United States Patent
Stefanchik et al.

[11] Patent Number: 6,015,416
[45] Date of Patent: Jan. 18, 2000

[54] SURGICAL ANASTOMOSIS INSTRUMENT

[75] Inventors: David Stefanchik, Mason; David L. Hamann, Cincinnati; John B. Flege, Jr., Cincinnati; Douglas N. Ladd, Cincinnati; J. Renee Lupton, West Chester, all of Ohio; James A. Craft, Lexington, Ky.

[73] Assignee: Ethicon Endo-Surgery, Inc., Cincinnati, Ohio

[21] Appl. No.: 09/031,346

[22] Filed: Feb. 26, 1998

[51] Int. Cl.$^7$ .................................................. A61B 17/04
[52] U.S. Cl. .......................... 606/144; 606/143; 606/145; 606/158; 606/1; 606/213; 606/216
[58] Field of Search ........................... 606/144, 139–143, 606/145–159, 213–216, 1; D15/69, 72, 66

[56] References Cited

U.S. PATENT DOCUMENTS

| | | | |
|---|---|---|---|
| 3,019,789 | 2/1962 | Whitehill et al. | 128/305 |
| 3,316,914 | 5/1967 | Collito | 128/334 |
| 3,561,448 | 2/1971 | Peternel | 128/334 |
| 4,204,541 | 5/1980 | Kapitanov | 128/334 |
| 4,345,600 | 8/1982 | Rothfuss | 128/334 |
| 4,366,819 | 1/1983 | Kaster | 128/334 |
| 4,368,736 | 1/1983 | Kaster | 128/334 |
| 4,470,415 | 9/1984 | Wozniak | 128/334 |
| 4,593,693 | 6/1986 | Schenck | 128/334 |
| 4,657,019 | 4/1987 | Walsh et al. | 128/334 |
| 4,749,114 | 6/1988 | Green | 227/19 |
| 4,773,420 | 9/1988 | Green | 128/334 |
| 4,803,984 | 2/1989 | Narayanan et al. | 128/334 |
| 4,915,107 | 4/1990 | Rebuffat et al. | 606/144 |
| 4,917,114 | 4/1990 | Green et al. | 227/179 |
| 4,930,502 | 6/1990 | Chen | 606/150 |
| 4,931,057 | 6/1990 | Cummings et al. | 606/153 |
| 4,997,439 | 3/1991 | Chen | 606/216 |
| 5,041,127 | 8/1991 | Troutman | 606/223 |
| 5,089,008 | 2/1992 | Chen | 606/216 |
| 5,188,636 | 2/1993 | Fedotov | 606/144 |
| 5,356,424 | 10/1994 | Buzerak et al. | 606/223 |
| 5,411,481 | 5/1995 | Allen et al. | 606/144 |
| 5,425,737 | 6/1995 | Burbank et al. | 606/144 |
| 5,520,703 | 5/1996 | Essig et al. | 606/148 |
| 5,545,148 | 8/1996 | Wurster | 604/223 |
| 5,562,685 | 10/1996 | Mollenauer et al. | 606/144 |
| 5,571,090 | 11/1996 | Sherts | 606/144 |
| 5,695,504 | 12/1997 | Gifford, III et al. | 606/153 |

FOREIGN PATENT DOCUMENTS

| | | | |
|---|---|---|---|
| 1181563 | 2/1970 | United Kingdom | A61B 17/11 |
| WO 95/17128 | 6/1995 | WIPO | A61B 17/11 |
| WO 97/12555 | 4/1997 | WIPO | A61B 17/11 |

*Primary Examiner*—Michael Buiz
*Assistant Examiner*—Lien Nao
*Attorney, Agent, or Firm*—Dean Garner

[57] ABSTRACT

In accordance with the present invention, there is provided a surgical device for attaching a first hollow organ to a second hollow organ and creating a passageway therebetween. The device includes a first member comprising a first prong for entering a wall of the first hollow organ and a second prong for entering a wall of the second hollow organ. The prongs each have a proximal end which attaches to the first member and a distal end extending therefrom. The device further includes a second member having a plow for incising at least one of the hollow organs so as to create a passageway between the hollow organs. The second member further includes a plurality of needle paths on either side of the plow for guiding a needle through the walls of the hollow organ on either side of the passageway. The device further includes a means for driving a needle, having a suture attached thereto, so as to attach the hollow organs together. Lastly, the device includes a frame for coupling the first member and the second member together in operational engagement.

25 Claims, 17 Drawing Sheets

SURGICAL ANASTOMOSIS INSTRUMENT

FIELD OF THE INVENTION

The present invention relates, in general, to devices and methods which facilitate the anastomosis of hollow organs of the body. More particularly, it relates to vascular anastomosis devices incorporating sutures for joining a graft blood vessel to a target blood vessel such as the aorta or coronary artery.

BACKGROUND OF THE INVENTION

Anastomosis, the surgical formation of a passage between two normally distinct organs or spaces, is a critical part of many surgical procedures. This is particularly true for coronary artery bypass graft (CABG) procedures in which one or more graft vessels are joined to coronary arteries. The distal end of the graft vessel is typically joined to the coronary artery distal to the stenosed or blocked portion of that artery, in order to improve the blood supply to the myocardium. The graft vessels normally used include the saphenous vein of the leg and the radial artery of the arm. After the graft vessels are harvested, they are cut to the correct length, and then joined on their proximal ends to a blood supply vessel, usually to the aorta. Thereafter, the graft's distal end is attached to the coronary artery. In an alternative procedure, the internal mammary artery (IMA) is used as a graft vessel. In this procedure the artery is temporarily clamped, severed at a location allowing enough length to be redirected towards the heart, dissected from the chest wall and arterial side branches, and then the distal end (pedicle) is attached to the left anterior descending coronary artery (LAD) to improve or restore blood flow to the myocardium of the heart. In this case, the anastomosis (the suture attachment) is made only at the distal end, or pedicle, of the IMA.

For the grafting procedures mentioned above, the type of vascular anastomosis used is typically referred to as an end-to-side type. That is, the open end of the graft vessel is attached to the side of the target vessel. However, other types of anastomosis are used as well. The end-to-end type of anastomosis is common for joining together larger hollow organs such as bowel, but can also be used for heart bypass procedures, especially for cases where the arterial flow is completely occluded by the stenosis in the diseased artery.

Some surgeons choose to complete all the proximal anastomoses to the aorta before commencing the distal anastomoses to the coronary arteries. In contrast, others choose to complete the distal anastomoses first. Regardless of the order, when undertaking the distal anastomoses to the coronary artery, it is important that the vessel graft be held steady and adjacent the coronary artery, with a minimum of vascular trauma and a minimum of visual and surgical obstruction by instruments in the narrow operative field.

Currently vascular anastomosis is accomplished by hand suturing with a tiny, curved needle and very fine suture filament. The suturing method, however, is very time consuming and requires several minutes per anastomosis, even for an experienced surgeon. In some cases the blood flow in the newly joined vessels may be poor, and the surgeon must remove the stitches and repeat the suturing procedure. In surgical procedures involving multiple bypass grafts, the time accumulated for doing the suturing is very substantial, putting the patient at risk and increasing the cost of the surgical procedure.

Hand suturing also requires a high level of skill and is not easily mastered by many surgeons. The preferred type of suturing method for the anastomosis of blood vessels is where the needle is passed through the wall of the first vessel (such as the coronary artery) from the inside to the outside, and then passed from the outside to the inside of the second vessel (such as the graft vessel), so that when the suture is drawn tight, the inside walls of the vessel come together, intima-to-intima. This is to insure that the vessels heal together properly with a smooth layer of endothelial cells formed on the inside of the anastomosis. A single stitch would first be done in this manner at each of the heel and toe locations of the anastomosis, and then a running stitch would be made on each half of the anastomosis between the heel and toe along the periphery of the anastomosis.

It is especially difficult to suture if the anastomosis site is not easily accessed or viewed. For the standard CABG procedure, access to the heart is obtained via a median sternotomy in which the rib cage is split longitudinally on the midline of the chest, and the left and right rib cages are spread apart. Less traumatic means of access are becoming more widely used in recent years, including a cardiac procedure known as MIDCAB (Minimally Invasive Direct Coronary Artery Bypass). In one version of a MIDCAB, access to the heart is obtained by using a small, left thoracotomy (incision between the ribs on the left chest) directly above the heart. In this procedure, the surgeon's access to the heart and visibility of it are significantly reduced, and hand suturing is even more difficult than when using a median sternotomy. Other new developments in the surgical procedures have made conventional suturing even more difficult. More and more surgeons are operating on a beating heart to avoid the complications associated with using a heart lung bypass machine.

A number of devices for augmentation of the suturing techniques have been developed. These devices attempt with varying degrees of success to reduce the difficulty in repeatedly passing a needle and thread through the vascular walls. Recent examples are found in U.S. Pat. 5,571,090 issued to Sherts on Nov. 5, 1996, U.S. Pat. No. 4,803,984 issued to Narayanan on Feb. 14, 1989, and U.S. Pat. No. 5,545,148 issued to Wurster on Aug. 13, 1996. However, these devices have a number of disadvantages. In Sherts and Narayanan, the individual stitches must still be made one at a time, and therefore the procedure is still tedious and time consuming. The working ends of the Wurster and Sherts devices appear to obstruct the view of the needle tip and so precise placement of the stitch might be difficult in some situations.

Surgical staplers are widely used for the end-to-end or side-to-side anastomosis of large, hollow organs and are often easier to use than sutures. The two types of surgical staplers used in such procedures are the circular stapler and the linear cutting stapler. Both of these kinds of devices require that the stapling implements of the distal ends be inserted inside of the hollow organs to be joined together. However, such stapling devices which are small enough to be used inside blood vessels and which are still effective are not currently available to surgeons.

For any surgical device used for vascular anastomosis, it is extremely important that both the graft and the target vessel not be manipulated to the extent that significant trauma to the vessels occurs. Again, this is to insure that the vessels heal together properly and a smooth passage between them is created. Current methods of vascular anastomosis of a graft to the coronary artery require that blood flow be temporarily stopped using some kind of clamping device on each vessel proximal to the anastomosis site. These clamping devices can risk injury to the artery, thus comprising the long term viability of the vessel to maintain blood flow.

Because of the aforementioned considerations, there has been a need to provide a surgical device for facilitating a suture anastomosis of very small hollow organs, such as blood vessels. There has been a need to have such a device which is easy to operate and can perform the anastomosis quickly and efficiently. There has also been a need to have such a device which can allow blood flow to be maintained during the joining of the blood vessels. There has also been a need for such a device that requires minimal manipulation of the blood vessels. Such a device should allow rapid healing of the endothelial lining inside the blood vessels, and allow the vessels to be joined together intima-to-intima. Such a device should also be adaptable for use during traditional, open cardiac procedures (CABG) as well as in minimally invasive procedures such as MIDCAB procedures. The present invention provides such a device.

SUMMARY OF THE INVENTION

In accordance with the present invention, there is provided a surgical device for attaching a first hollow organ to a second hollow organ and creating a passageway therebetween. The present invention may be use for both the end-to-side and the side-to-side variations of anastomosis. The device includes a tissue clip comprising a joining member, a first prong for entering a wall of the first hollow organ and a second prong for entering a wall of the second hollow organ. The prongs each have proximal ends which are attached to the joining member and distal ends extending therefrom. At least one of the prongs is pivoted at its proximal end so that the vessels can be moved into an abutting relationship. The device further includes a cassette having a plow for incising the vessel walls to create a passageway therebetween. The plow also guides a pair of spiral needles with sutures attached thereto through the walls of the vessels on either side of the passageway. The device further includes a means for driving the spiral needles so as to attach the vessels together. Lastly, the device includes a frame for coupling the tissue clip and the cassette together in operational engagement.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

The drawings are not necessarily to scale.

DETAILED DESCRIPTION OF THE INVENTION

In the following detailed description of the present invention, a description of how the invention is used to create an end-to-side anastomosis between two blood vessels is provided concurrently. The same steps described may also be followed for creating a side-to-side anastomosis, and are not limited to only blood vessels, but may be used for joining other types of hollow organs as well.

Figure 1:
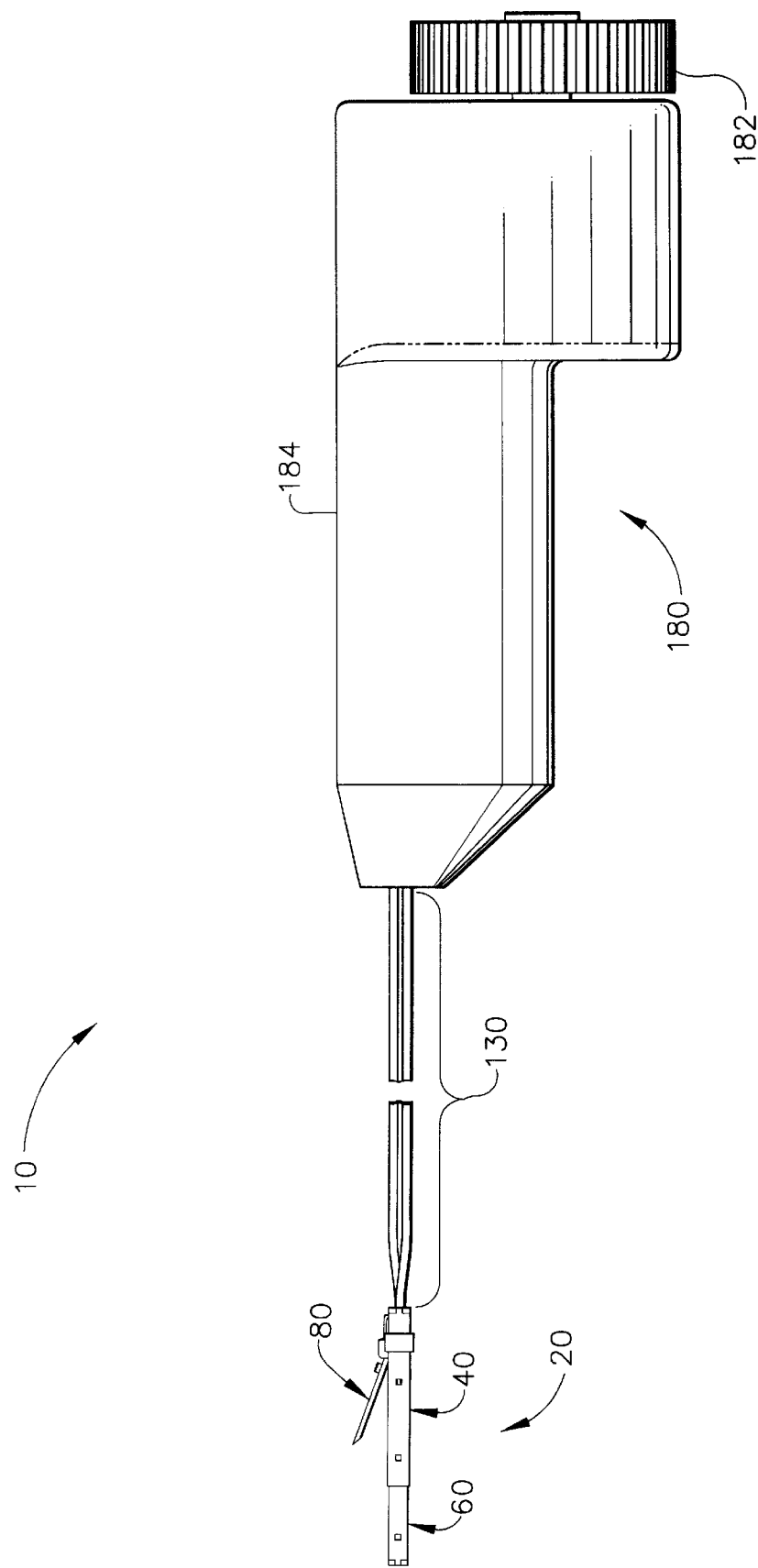
FIG. 1 is a front elevational view of the surgical device of the present invention.

Referring now to the drawings wherein like numerals indicate the same element throughout the views, there is shown in FIG. 1 a preferred embodiment of the present invention, surgical device 10. Surgical device 10 includes a handle 180 with a control knob 182, a drive section 130 attached to the distal end of the handle, and an implement 20 attached to the distal end of the drive section. The implement includes a tissue clip 80, a frame 40, and a cassette 60. In this embodiment, the drive section 130 is flexible in order to facilitate the placement of the implement at the surgical site.

Figure 2:
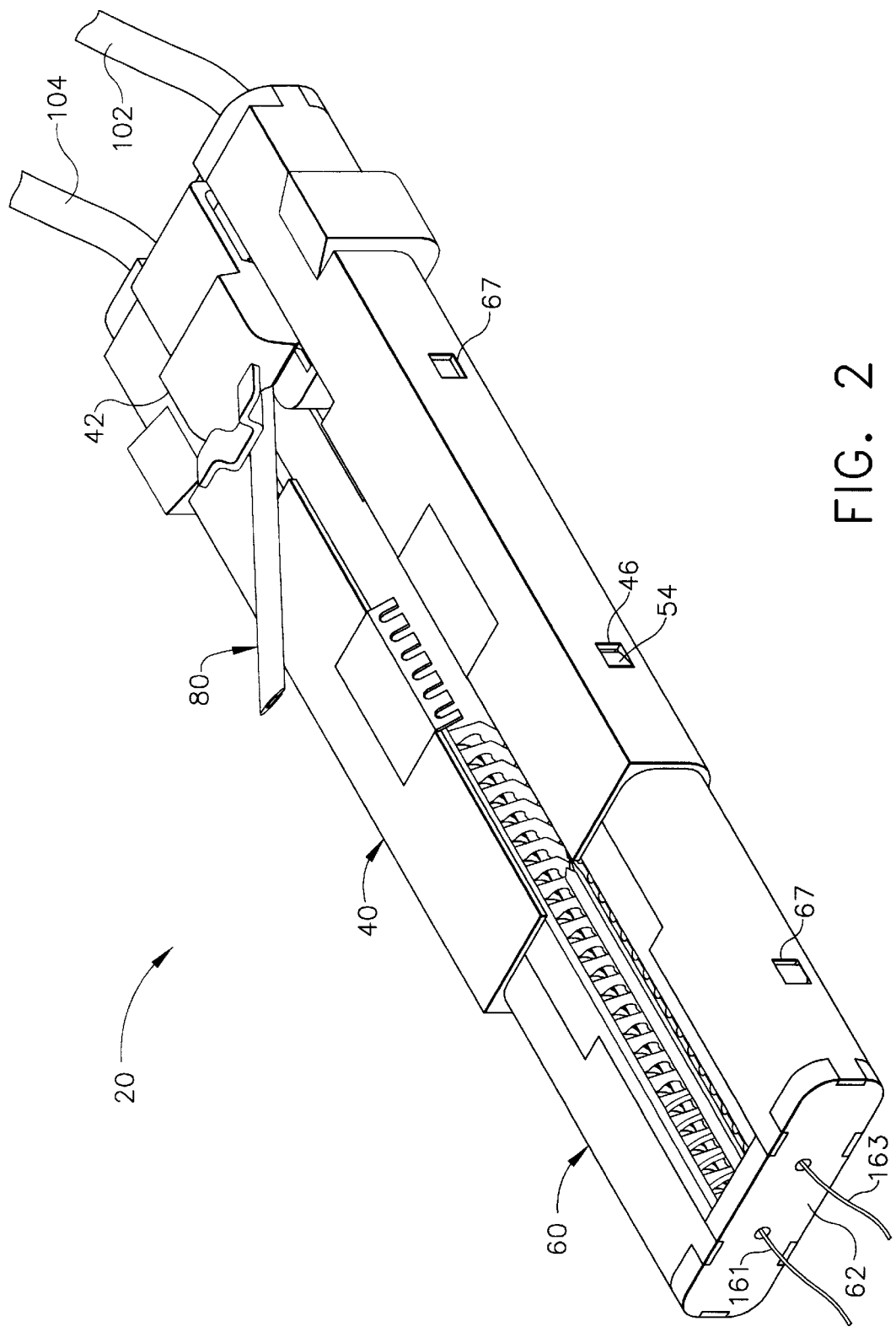
FIG. 2 is an isometric view of the implement of the surgical device.

FIG. 2 is a isometric view of the implement 20 of the surgical device 10 as the implement may be assembled prior to use. The cassette 60 is shown partially inserted into the frame 40. Right drive member 104 and left drive member 102 of the drive section 130 are attached to the proximal end of the frame 40. Each of these drive members transmits a torque from the control knob 182 of the handle 180 to the implement 20. A right surgical suture filament 161 and a left surgical suture filament 163 are shown coming out of the end cover 62 of the cassette 60. A tissue button 42 on the frame 40 is used to move the tissue clip 80 as will be described later.

Figure 3:
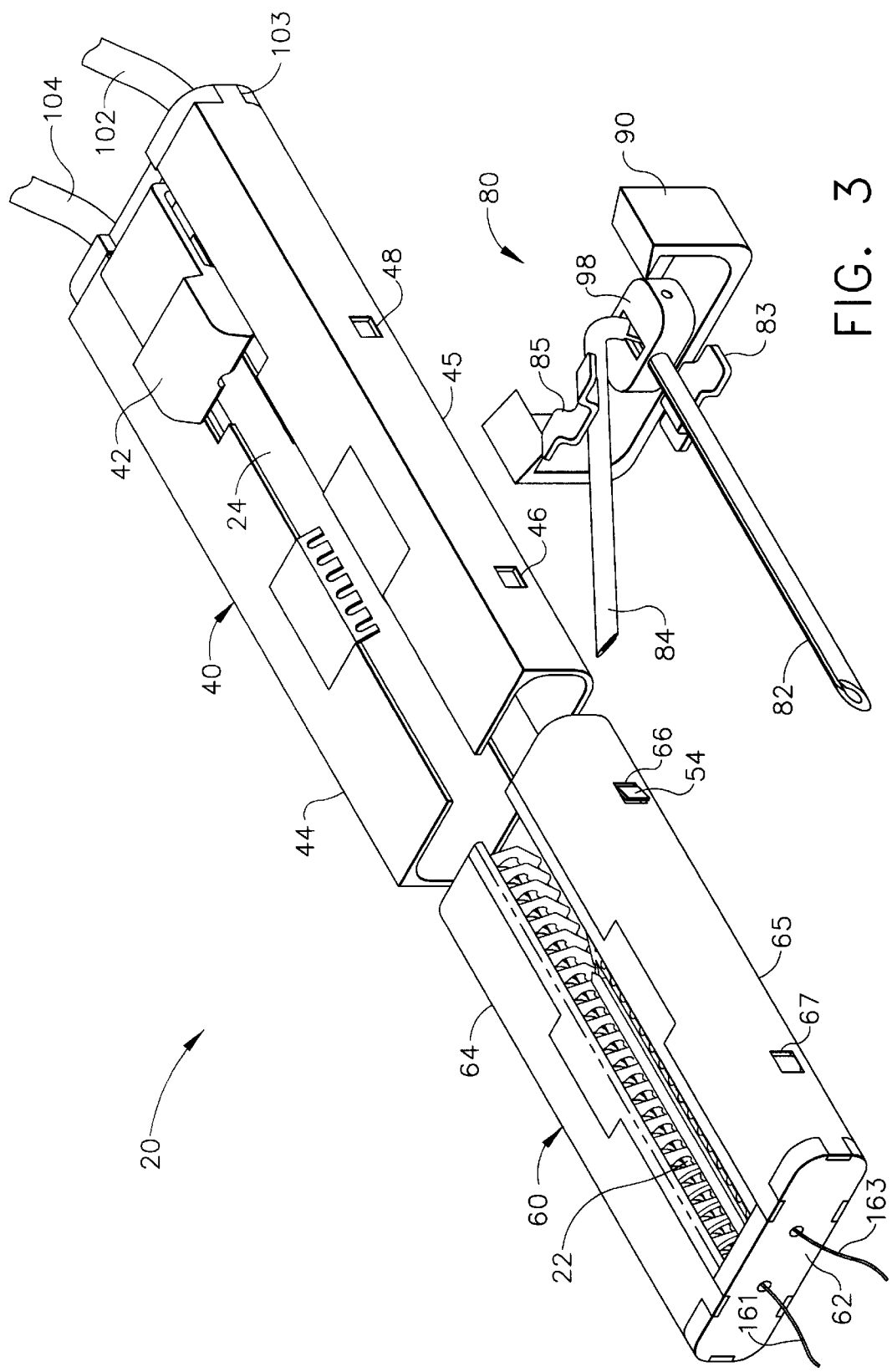
FIG. 3 is an exploded isometric view illustrating the details of the implement of the surgical device.

FIG. 3 shows the implement 20 of FIG. 2 with the cassette 60 (also referred to as a second member) and the tissue clip 80 (also referred to as a first member) disassembled from the frame 40. The cassette 60 has a right cassette housing 64 and a left cassette housing 65 joined together on their distal ends by the end cover 62, and forming a longitudinal cassette opening 22. The cassette 60 has a generally rectangular cross section which slidably fits into the distal end of frame 40. The cassette contains the work portion of the implement 20 for creating the anastomosis of the two blood vessels.

Still referring to FIG. 3, the frame 40 consists of a right frame housing 44 and a left frame housing 45 joined together at their proximal ends by a plate 103, and forming a longitudinal frame opening 24. The left and right drive members, 102 and 104, enter the frame through the plate 103. Tissue button 42 is captured between the left and right frame housings, 45 and 44. The first detent hole 46 and the second detent hole 48 are aligned to receive the first detent 66 of the cassette 60 in order to controllably position the cassette in the frame 40 during the use of the surgical device 10.

Also in FIG. 3, the tissue clip 80 consists of a first prong 82 and a second prong 84, each prong having a tip designed for entering through a blood vessel wall. The prong tips may be used to pierce directly into the vessel wall, or a small hole could first be made in the vessel wall with a scalpel or other surgical device, and then the prong could be gently inserted. What's important to note, however, is that either method could be used while blood flow through the vessel is maintained, because the hole required for the prong is very small and mostly occluded by the prong. Slight oozing of blood is normally acceptable by surgeons during bypass procedures.

As can be seen in FIG. 3, the prongs, 82 and 84, are C-channels made preferably from a stainless steel. On the first prong 82 is attached a first tissue stop 83. On second prong 84 is attached a second tissue stop 85. The tissue stops prevent the prongs from being inserted too far into the blood vessels. The tissue clip 80 also includes a snap-on beam 90 for removably attaching the tissue clip to the frame 40 of the implement 20 as depicted in FIG. 2.

Figure 4:
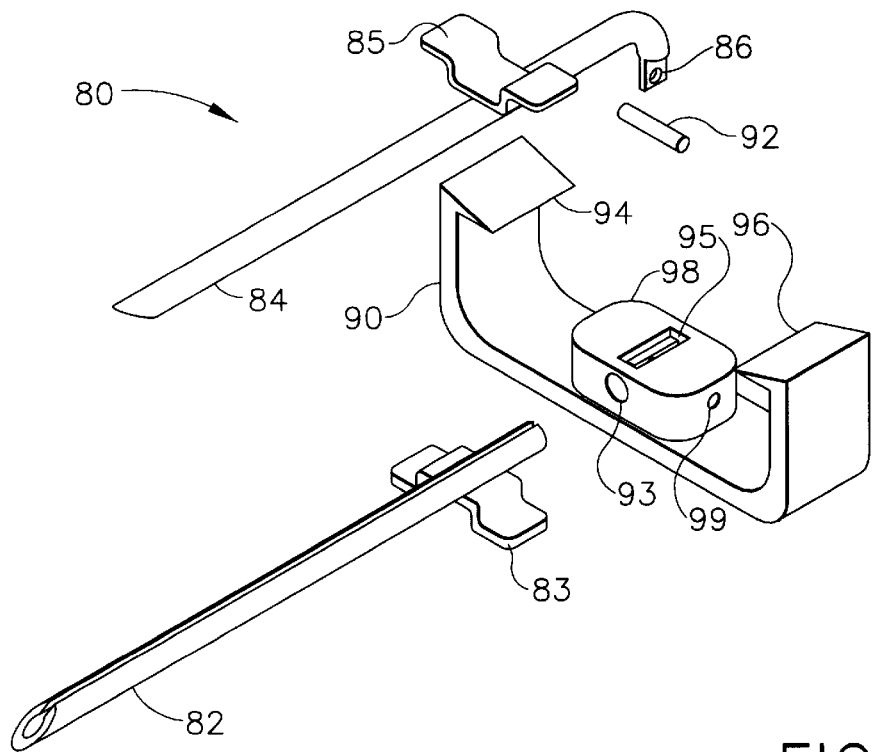
FIG. 4 is an exploded isometric view of the tissue clip of the implement of the surgical device.

Turning now to FIG. 4, the tissue clip 80 is shown in an exploded, perspective view. The distal end of the first prong 82 fits tightly into prong hole 93. The distal end of second prong 84 attaches pivotably to prong block 98 (also referred to as a joining member) into prong slot 95, and is retained by prong pivot pin 92 fitting tightly in pin hole 99. As a result, the distal end of the second prong 84 is moveable towards and away from first prong 82.

Figure 5:
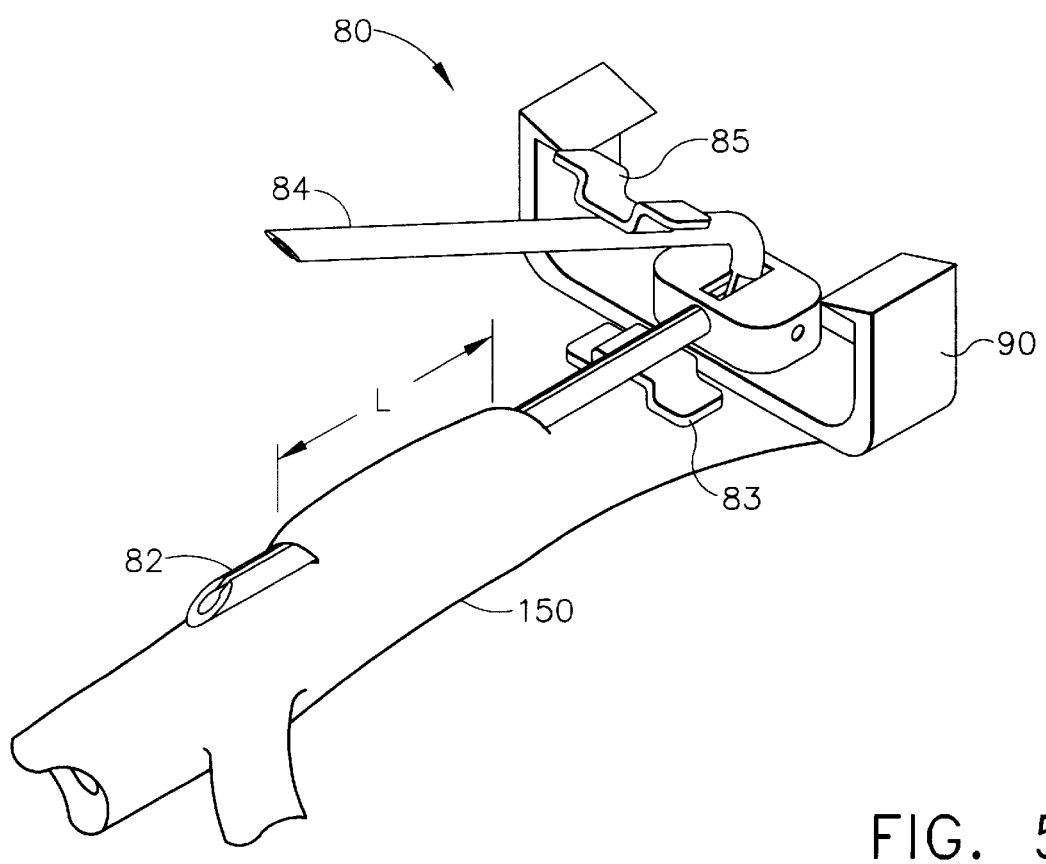
FIG. 5 is an isometric view of the tissue clip of the implement of the surgical device placed into a target blood vessel.

FIG. 5 depicts the tissue clip 80 inserted into a target blood vessel 150. The length "L" represents the portion of the target blood vessel 150 to be anastomosed to the graft blood vessel (not shown).

Figure 6:
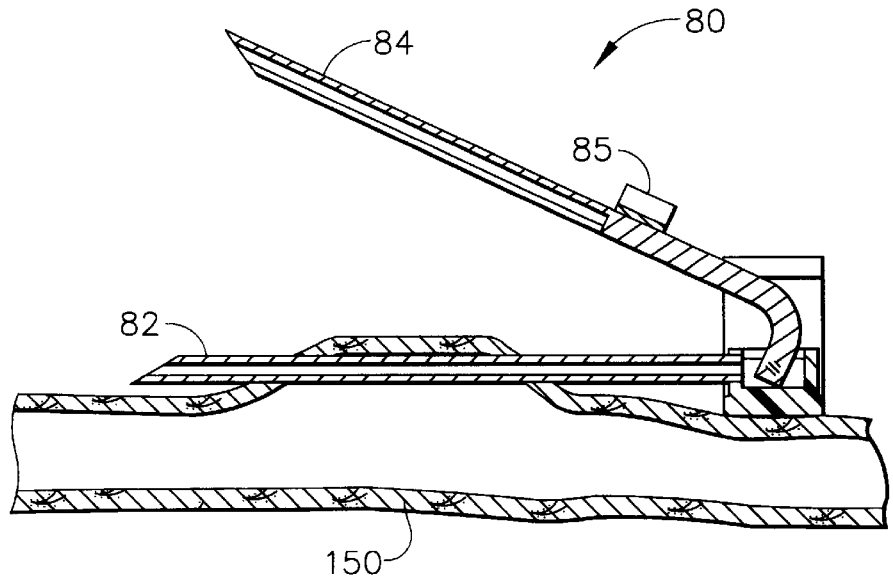
FIG. 6 is a side elevational view in section of the tissue clip and the target blood vessel depicted in FIG. 5.

In FIG. 6, a sectional view of the tissue clip 80 inserted into the target blood vessel 150 depicts how blood flow through the vessel is substantially maintainable because the first prong 82 is slender relative to the vessel.

Figure 7:
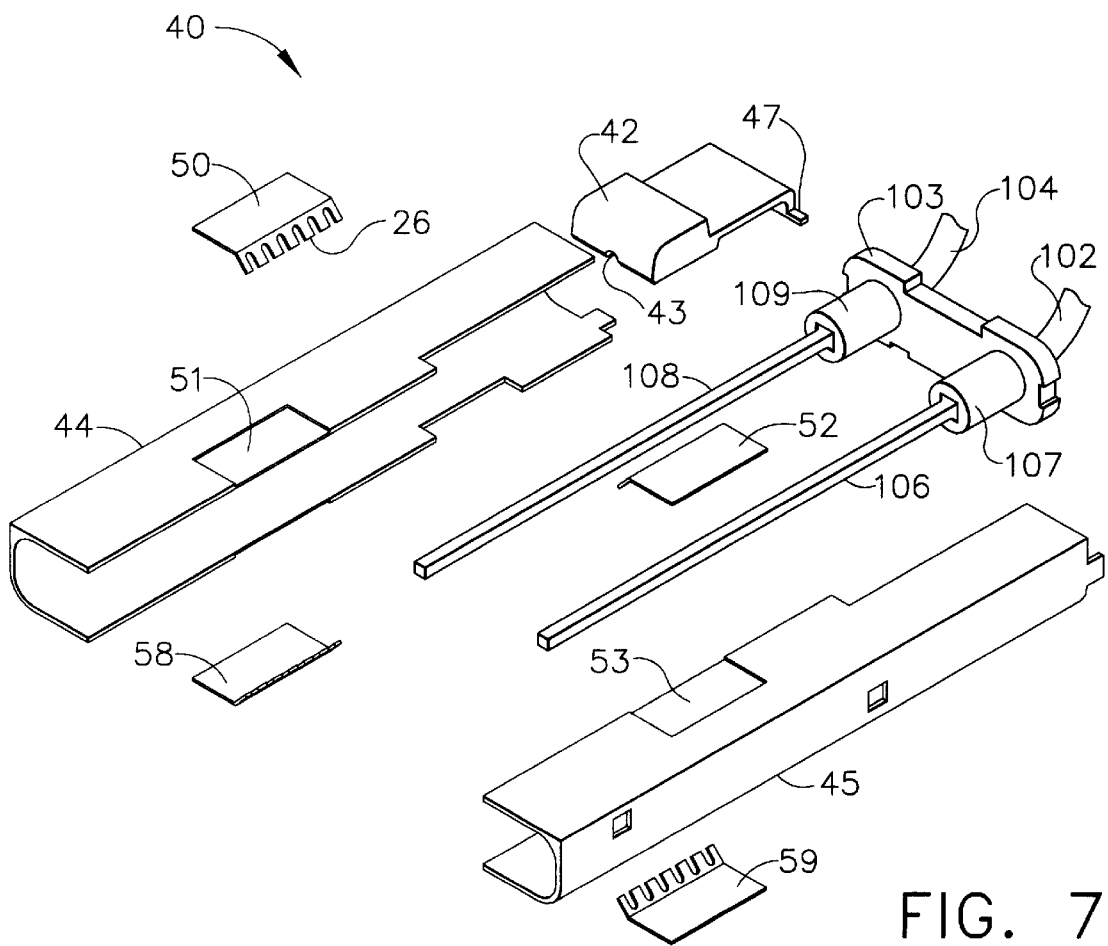
FIG. 7 is an exploded isometric view of the frame of the implement of the surgical device.

FIG. 7 is an exploded isometric view of the frame 40 of the implement 20 of the surgical device 10. This view reveals a left drive shaft 106 and an associated left drive coupler 107 attached to the left drive member 102, and rotatably captured on plate 103. Likewise, a right drive shaft 108 and an associated right drive coupler 109 are attached to right drive member 104 and are rotatably captured on plate 103. Drive shafts 106 and 108 are preferably made from stainless steel and have a uniformly square cross section along their lengths. Also provided on frame 40 is a right upper tissue clamp 50 which attaches to right upper clamp recess 51 of right frame housing 44. A left upper tissue clamp 52 attaches to left upper clamp recess 53 of left frame housing 45. Similarly left and right lower tissue clamps, 58 and 59, are mounted to the underside of frame 40. Tissue clamps 50, 52, 58, and 59 are preferably made from stainless steel and each contains a plurality of flutes 26 along one edge and extending into the longitudinal opening 24 (see FIG. 3) of the frame 40. Tissue button 42 is shown with two tissue button tabs 47 for retention inside frame 40. A longitudinal, tissue button groove 43 is provided for a reason to be described.

Figure 8:
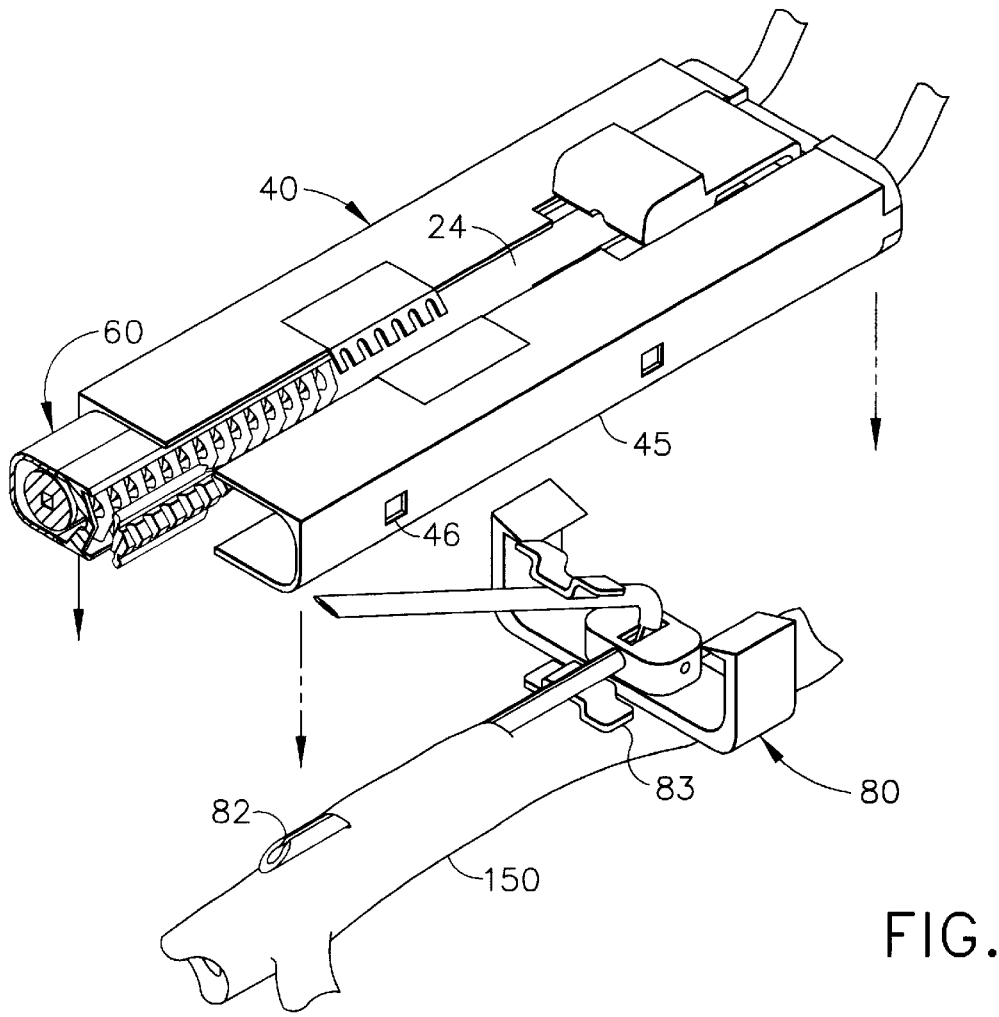
FIG. 8 is an isometric view of the frame depicted in FIG. 7 being placed together with the tissue clip and blood vessel depicted in FIG. 5, also showing a partial view of the cassette inserted into the frame.

Referring now to FIG. 8, the frame 40 containing the cassette 60 (partially cut away for clarity) is shown being placed onto the tissue clip 80 which is already inserted into target blood vessel 150. The cassette 60 has already been inserted into frame 40 at a location corresponding to when the left hook 54 (see FIG. 3) of the cassette 60 is in the first detent hole 46 of the left frame housing 45.

Figure 9:
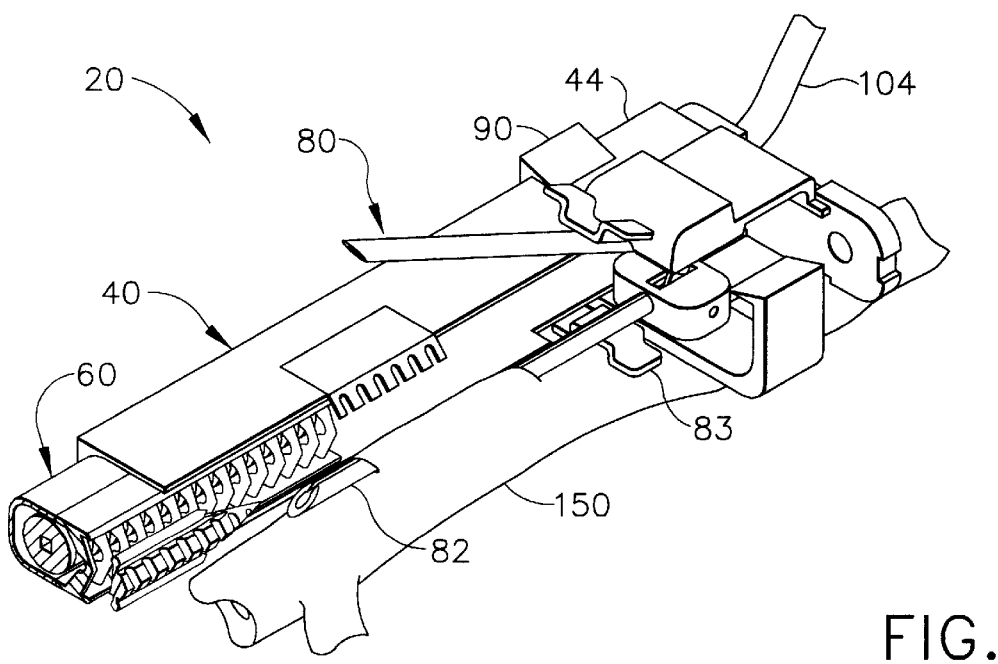
FIG. 9 is an isometric sectional view of the frame and cassette placed together with the tissue clip and blood vessel.

In FIG. 9, the frame 40 is attached to the tissue clip 80, aligning the target blood vessel 150 with the longitudinal opening 24 (see FIG. 8) of the frame. The left part of the implement 20 has been removed for clarity. The snap on beam 90 of the tissue clip 80 is shown gripping around the sides of the frame 40.

Figure 10:
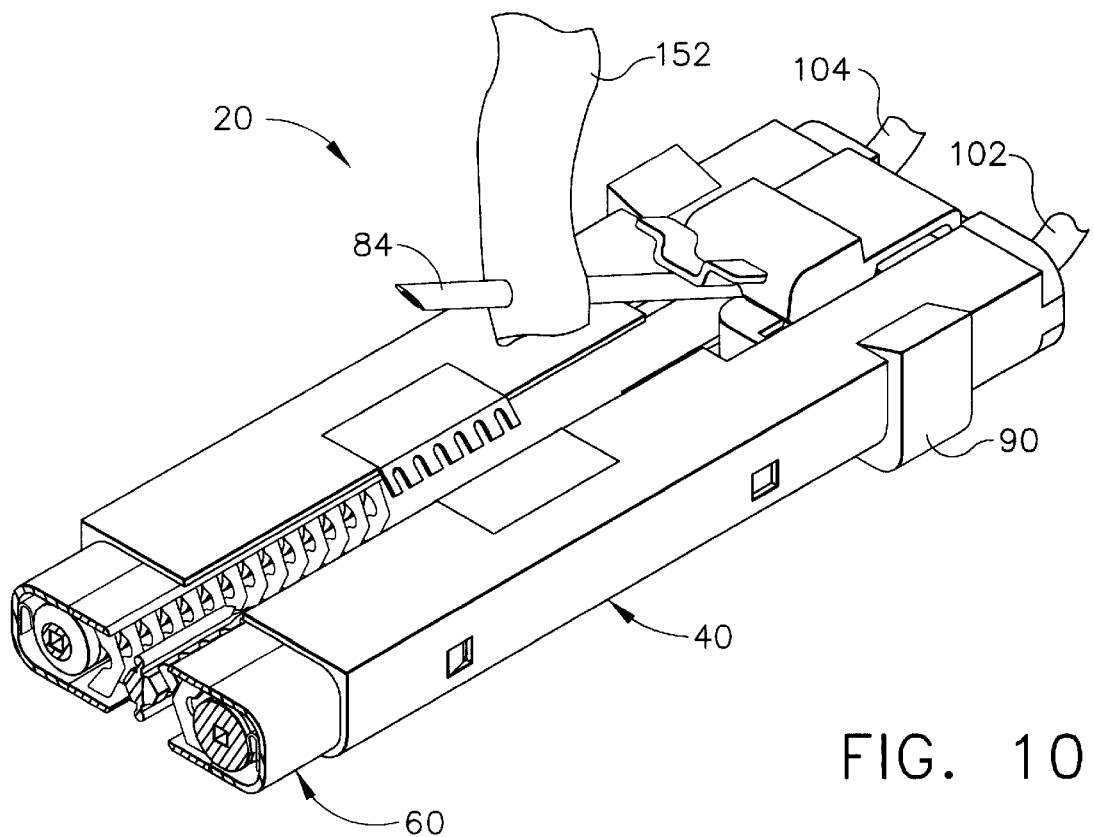
FIG. 10 is an isometric view of the implement of the surgical device, with a sectional view of the cassette, and showing the tissue clip inserted into a graft blood vessel.

Now turning to FIG. 10, the graft blood vessel 152 is shown placed onto the second prong 84 of the tissue clip 80. The cassette 60 is still located at the same position as in FIGS. 8 and 9. The second prong 84 is held in a center position between the right and left frame housings, 44 and 45 respectively, by the tissue bottom groove 43 of the tissue button 42. In this view, the graft vessel 152 is shown more or less as being placed onto the prong 84 so as to result in an end-to-side anastomosis with the angle between the joined vessels being about 90 degrees. An advantage of the present invention over some of the prior art is evident here, because clearly it is permissible for the surgeon to first trim the end of the graft vessel 152 with a beveled cut (other than perpendicular to the longitudinal axis of the vessel) and then to place the vessel onto the prong 84 at an angle favoring a more gradual approach to the junction with the target vessel.

Figure 11:
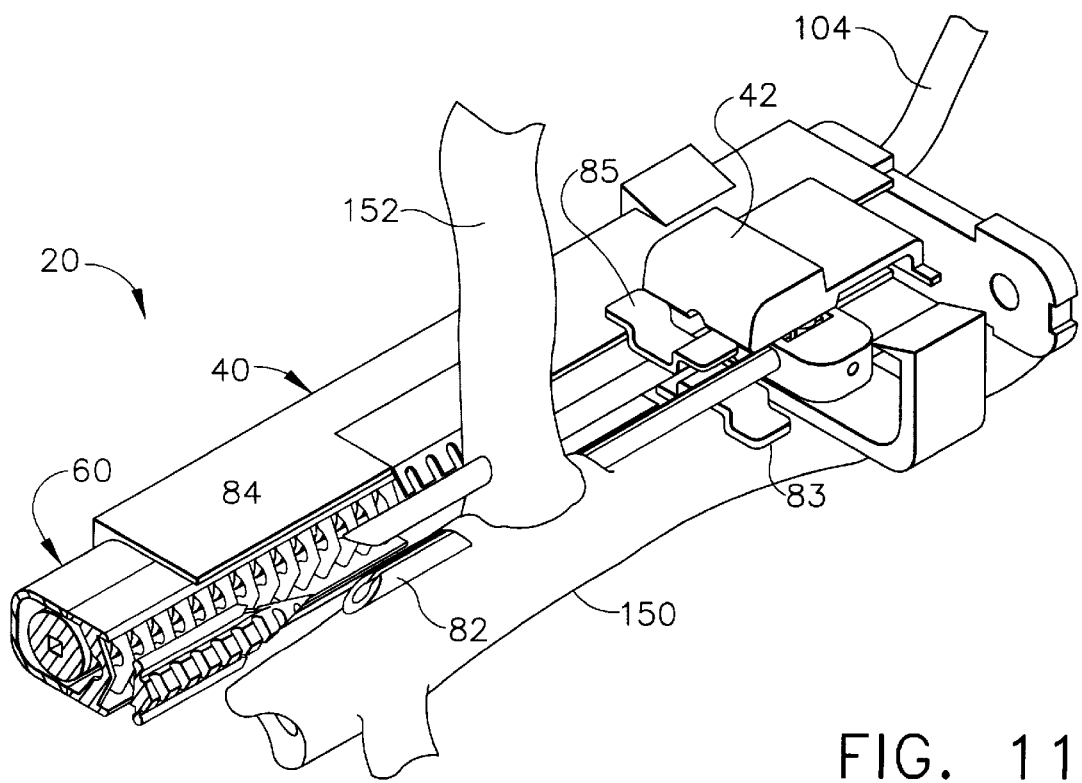
FIG. 11 is an isometric sectional view of the implement of the surgical device with the target and graft blood vessels held together in the end-to-side manner.

In FIG. 11, the tissue button 42 has been pushed by the user in the distal direction to cause the second prong 84 to move to a position where it is parallel with the first prong 82. As a consequence, the end of the graft blood vessel 152 has been brought into contact with the side of the target blood vessel 150. The flutes 26 of the upper tissue clamps 50 and 52 bear against the sides of the graft blood vessel 152 to help align and hold the graft vessel in the location shown. Similarly, the flutes 26 of the lower tissue clamps 58 and 59 bear against the sides of the target vessel 150 to help align and hold the target vessel in the location shown.

Figure 12:
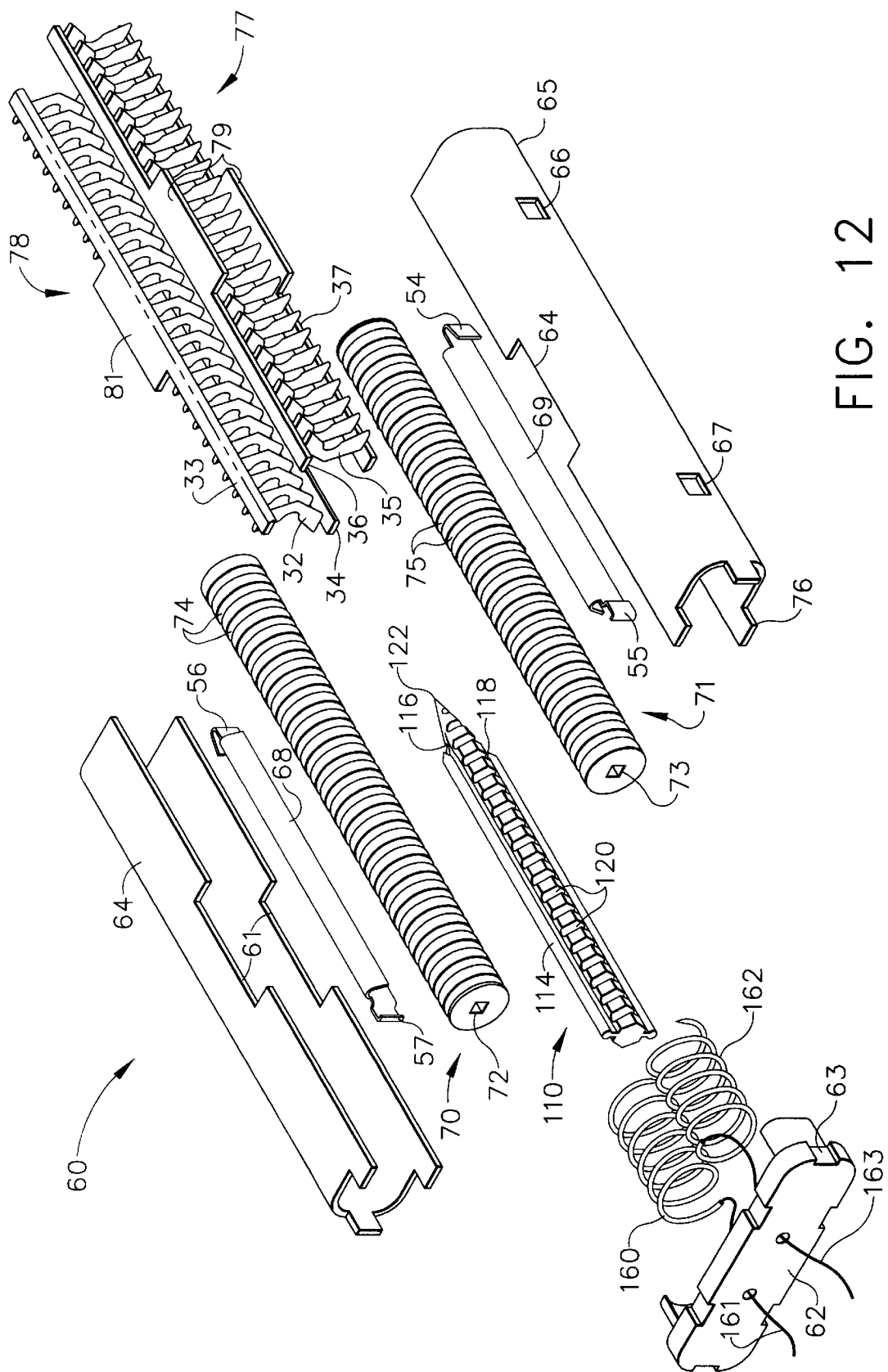
FIG. 12 is an exploded isometric view of the cassette, illustrating the details of the components.

FIG. 12 is an exploded isometric view of the cassette 60. As described earlier, the right and left cassette housings, 64 and 65 respectively, are joined at their distal ends by the end cover 62. End tabs 76 of each of the cassette housings fit into the end cover recesses 63 to insure the assembly is properly aligned. The internal, working portion of the cassette 60 comprises a left roller 71, a right roller 70, a left needle guide 77, a right needle guide 78, a left roller spring 69, a right roller spring 68, a plow 110, a left surgical spiral needle 162 attached to suture filament 163, and a right surgical spiral needle 160 attached to a right suture filament 161. The rollers, 70 and 71, are also referred to as drivers.

Associated with the right roller 70 is the right needle guide 78 containing a multiplicity of vertical ribs 32 evenly spaced apart along the length of the right needle guide 78 and connected to an upper rail 33 and a lower rail 34. Likewise on the left needle guide 77 is a multiplicity of vertical ribs 35 evenly spaced apart along the length of the left needle guide 77 and connected to an upper rail 36 and a lower rail 37. These vertical ribs, 32 and 35, are also referred to as needle paths. Each of the needle guides, 78 and 77, are preferably molded as one piece from a medical grade, rigid plastic. In addition, right needle guide 78 has a pair of right alignment tabs 81 to locate into a pair of right recesses 61 of the right cassette housing 64. The left needle guide 77 has a pair of left alignment tabs 79 to locate into a pair of left recesses 64 of the left cassette housing 65.

Still referring to FIG. 12, the left roller spring 69 is sandwiched between the left roller 71 and the left cassette housing 65. The right roller spring 64 is sandwiched between the right roller 70 and the right cassette housing 64. Left hook 54 of roller spring 69 hooks into first hole 66 of the left cassette housing 65, while left finger 55 of the left roller spring 69 locates into second hole 67 of the left cassette housing 65. A right hook 56 and a right finger 57 of the right roller spring 68 attach similarly to right cassette housing 64 (holes in right cassette housing are not visible). Each roller spring is formed so as to be compressible in a direction perpendicular to the longitudinal axis of the respective roller bearing against it. The roller springs, 68 and 69 are made from a stainless steel or other spring material.

The plow 110 shown in FIG. 12 is preferably made of a rigid, medical grade plastic but could also be made of a metal such as stainless steel. The plow 110 contains a plurality of grooves 120 spaced evenly along its length on each side. The plow 110 has an upper plow rail 114 and a lower plow rail 112 extending along most of its length as shown. On the proximal end of plow 110 is a plow point 122 which bisects an upper cutting edge 116 and a lower cutting edge 118. When the plow 110 is actuated as will be described, these cutting edges incise the tissue of the graft and target blood vessels, 152 and 150, to create a passageway between them. The grooves 120 serve as needle guides for the two surgical, spiral needles 161 and 162.

The right and left surgical spiral needles, 160 and 162 respectively, are made from surgical steel wire and have a plurality of windings of equal diameter. The left spiral needle 162 is wound in the opposite direction of the right spiral needle 160. The blunt ends of the spiral needles 160 and 162 are attached to suture filaments 161 and 163 respectively. A length of these suture filaments 160 and 162 extend out through the end cover through filament holes 166 and 167, respectively. As the spiral needles 160 and 162 are advanced in the proximal direction, the suture filaments 160 and 162 are partially drawn into the cassette 60.

As shown in FIG. 12, the right roller 70 and the left roller 71 are essentially hollow, circular cylinders with a multiplicity of annular grooves 74 evenly spaced apart along their lengths. The opposing side walls on the inside of each annular groove 74 is angled so as to form a V-shaped cross section as in a pulley for a V-belt used for automobiles, for example. This V-shape is advantageous to the present invention in that the engagement with the spiral needles, 160 and 162, are enhanced due to the wedging action of the annular grooves 74 onto the spiral needles. Each of the rollers 70 and 71 have a longitudinal, square hole, 72 and 73 respectively, extending through their entire length on the longitudinal axis. The rollers are preferably made from a medical grade, rigid plastic or from a stainless steel. The left and right rollers, 71 and 70, are coated with a microabrasive material such as synthetic diamond, real diamond, or silicon carbide, applied to the rollers with any of a number of bonding processes known to those in the art as. The coating is added in order to enhance the frictional engagement with the spiral needles, 160 and 162, and thus minimize slipping as each roller drives its respective spiral needle.

Figure 13:
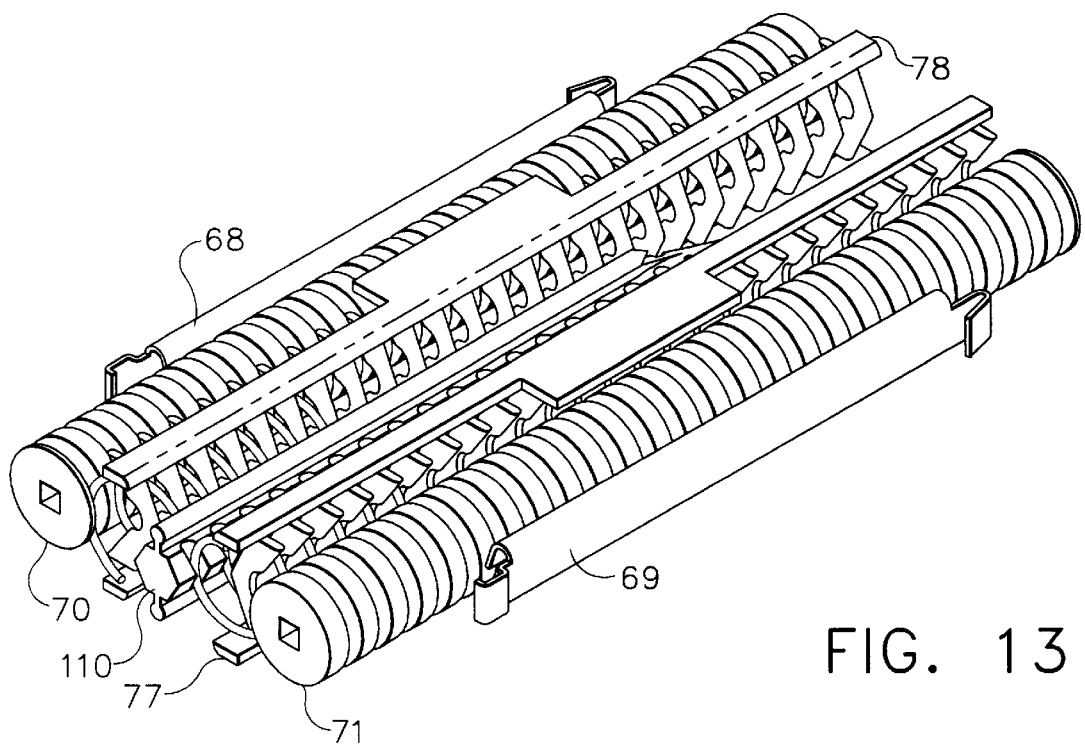
FIG. 13 is an isometric view of the internal portion of the cassette shown in their initial alignment (before firing)
Figure 14:
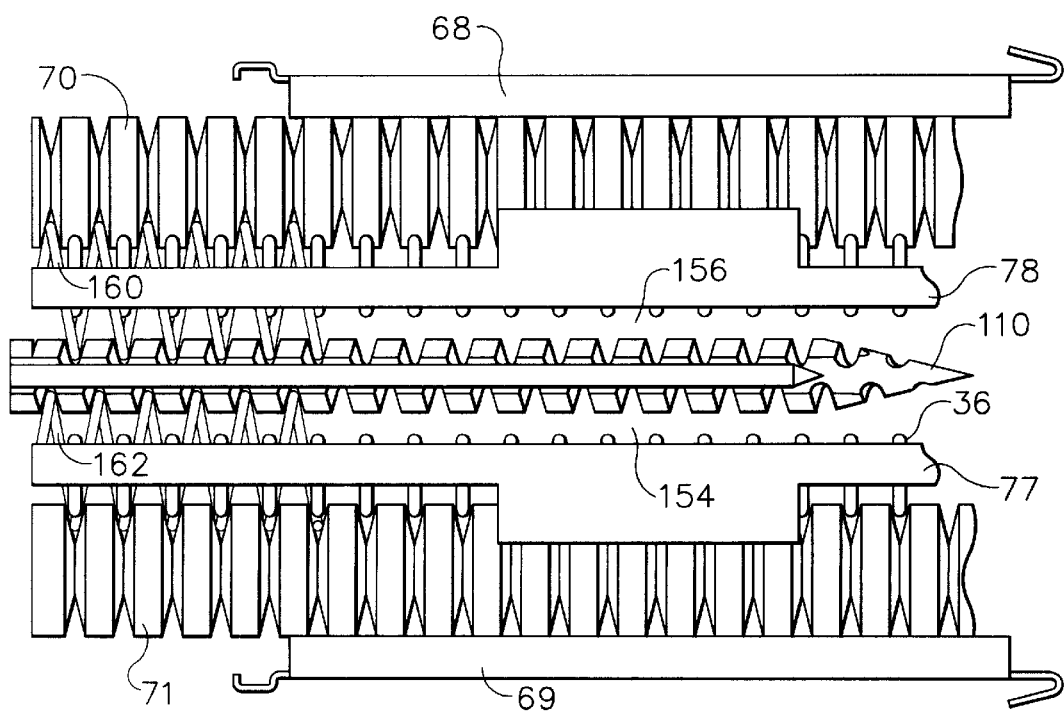
FIG. 14 is a top view of the internal portion of the cassette depicted in FIG. 13 showing the initial location of the two surgical, spiral needles.

FIG. 13 is a perspective view of the working portion of the cassette 60 as it would be assembled prior to actuation. FIG. 14 is a top view of the same working portion and shows the alignment of the windings of the left spiral needle 162, into the left roller grooves 75 of the left roller 71, and concurrently aligned in the grooves 120 of the plow 110. The windings of the spiral needle 162 also mesh with the vertical ribs 35 of the left needle guide 77. It can also be seen how the left roller spring 69 bears against the left roller 71 and serves to hold the spiral needle 162 between the left roller 71 and the plow 110. The rotation of the left roller 71 about its longitudinal axis therefore drives the spiral needle 162 to cause it to move longitudinally. The direction of the rotation would determine the direction of the longitudinal movement of the spiral needle 162. The left gap 154 between the left needle guide 77 and the plow 110 is where the left edges of the graft and target blood vessels, 152 and 150, would be held together. The left needle guide 77 and the plow 110 are stationary while the left roller 71 is rotated to advance the left spiral needle 162. The same arrangement is provided on the right side of the working portion of the cassette 60, with the exception that the windings of the right spiral needle 160 are out of phase with the windings of the left spiral needle 162. This is so the stitches created by the advancement of the left spiral needle 162 are staggered with respect to the stitches created by the right spiral needle 160.

Figure 15:
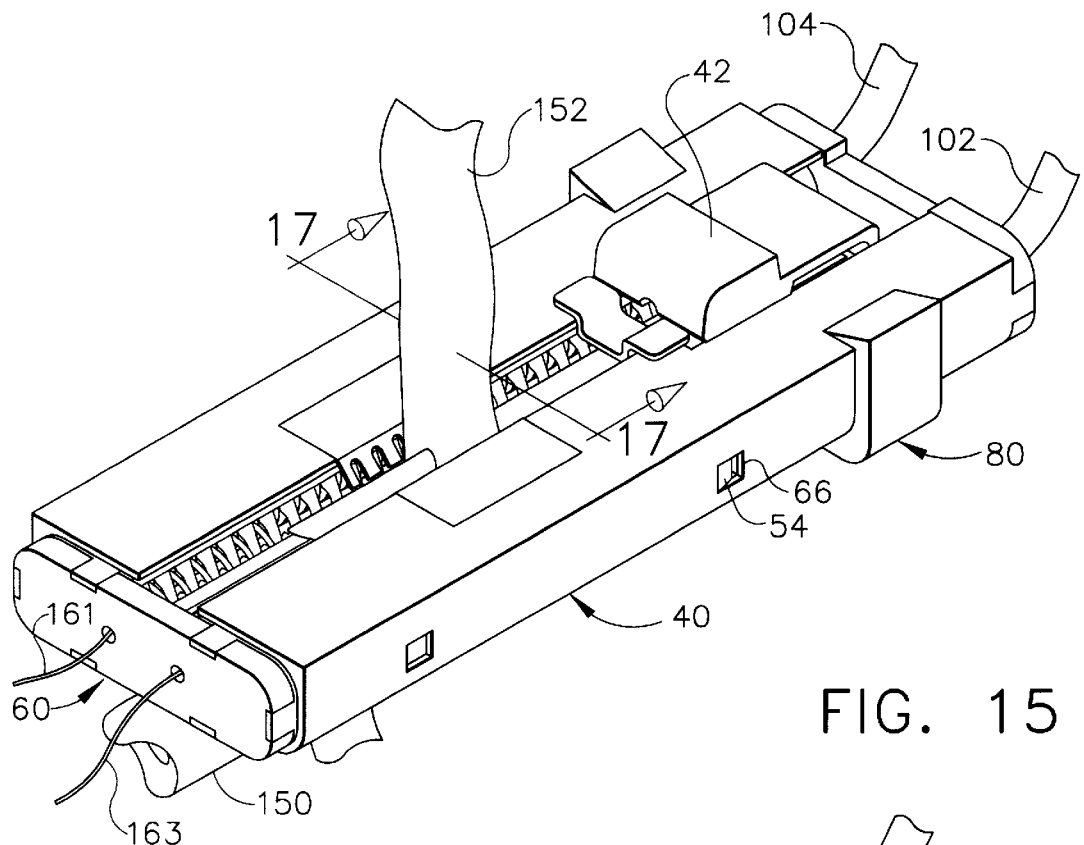
FIG. 15 is an isometric view of the implement of the surgical device holding together the target and graft blood vessels after the cassette has been completely pushed into the frame.
Figure 16:
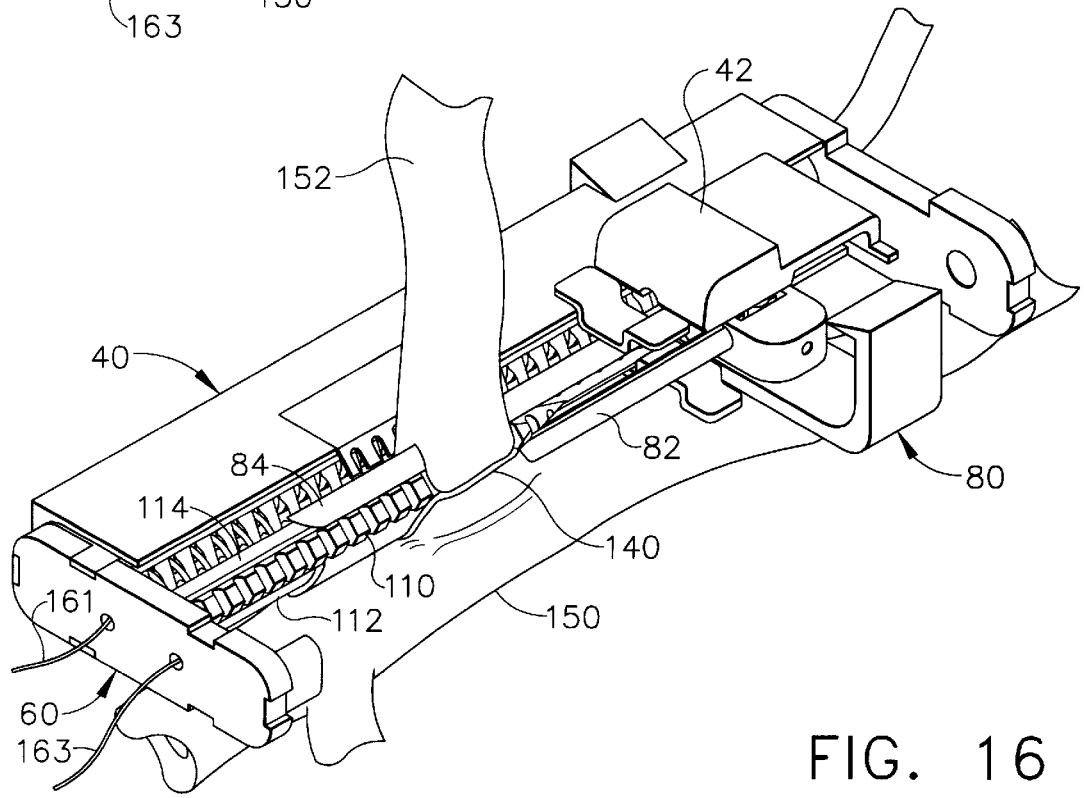
FIG. 16 is an isometric view of the implement depicted in FIG. 15, with part of the implement removed for clarity, showing more clearly the formation of a passageway between the target and graft blood vessels.

FIG. 15 is a view of the implement 20 as it is holding the graft and target blood vessels, 152 and 150, and after the cassette 60 has been pushed into the frame 40 to a second position. The left hook 54 clicks into left hole 66 at this position to provide feedback to the user that the cassette 60 is properly positioned. By pushing the cassette 60 into the frame 40, the plow 110 has been advanced in the proximal direction. The plow point 122 and upper and lower cutting edges, 116 and 118, have been pushed through the graft and target vessels at their juncture and created a passageway between them. In FIG. 16, the fully advanced plow 110 can be seen after it has cut through the vessels and created a left tissue junction 140 and a right tissue junction 142 (see FIG. 17). As the plow 110 advances through the tissue, the entire working portion of the cassette 60, including the spiral needles 160 and 162, moved axially as well, thus positioning the spiral needles near the graft and target blood vessels, 152 and 150.

Figure 17:
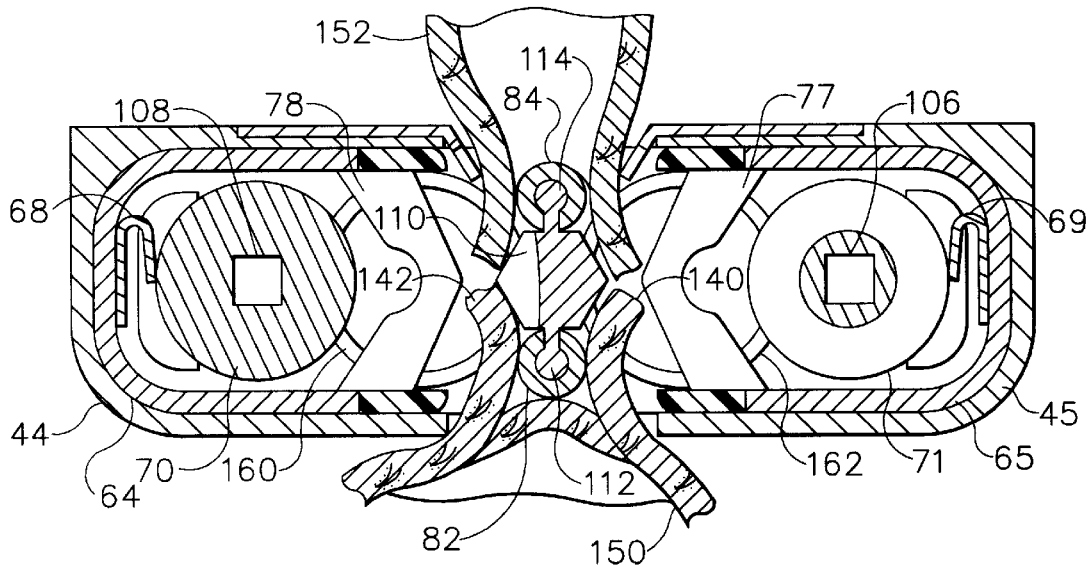
FIG. 17 is a sectional view of the distal portion and blood vessels taken along line 17—17 of FIG. 15.

FIG. 17 is a sectional view taken along line 17-17 of FIG. 15, looking distally (towards the spiral needles). Here it can be seen how the plowing action of the plow 110 has caused the edges of the graft and target vessel to evert partially to form the left and right tissue junctions, 140 and 142. It can also be seen how the longitudinal advancement of the rotating spiral needles will cause a series of stitches to be made through the tissue junctions, 140 and 142. The tissue junctions eventually become the peripheral edge of the passageway between the vessels. These tissue junctions must be held together firmly along their entire length as the spiral needles advance. This is accomplished by maintaining the close, parallel alignment of the first and second prongs, 82 and 84, of the tissue clip 80. In FIG. 17 is shown how the upper rail 114 of the plow 110 has inserted into the second prong 84 of the tissue clip 80. The lower rail 112 of the plow 110 has inserted into the first prong 82 of the tissue clip 80. This arrangement occurred as the plow 110 was advanced proximally by the user pushing the cassette 60 into the frame 40.

Figure 18:
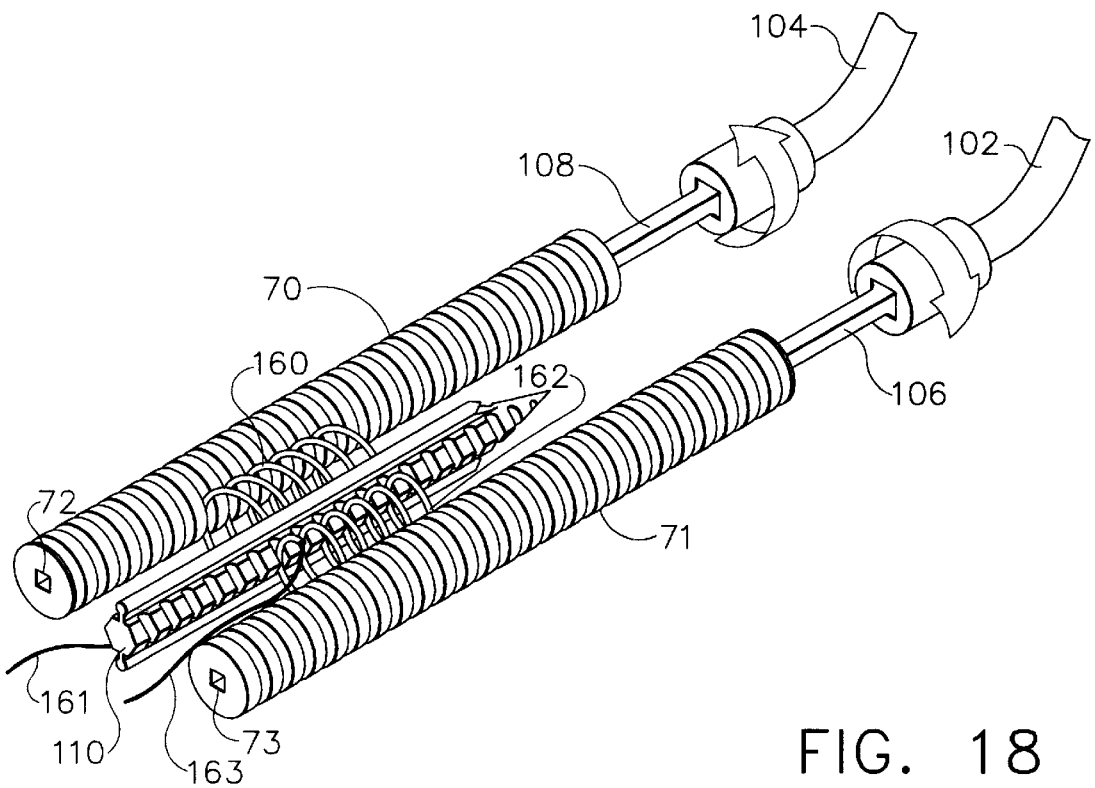
FIG. 18 is an isometric view of the rollers of the implement being rotated by flexible shafts in order to advance the two spiral needles.

In FIG. 18 is shown the left and right drive members, 102 and 104, engaging with the left and right rollers, 71 and 70. The left drive shaft 106 slides freely into the left roller hole 73, but because of the non-circular shape of the left roller hole 73 and the similarly shaped drive shaft 106, the rotation of the driveshaft is transmitted to the roller in the direction shown. The same arrangement is provided on the right side, except the right roller 70 is rotated in the opposite direction as the left roller 71.

The primary reason it is desirable to rotate the rollers, 71 and 70, and hence the spiral needles, 162 and 160, in opposite directions is to maintain good suturing technique. When the surgeon uses a hand suturing technique, the surgeon tries to avoid passing a needle through the coronary artery wall from the outside to the inside, but rather passes the needle from the inside to the outside. This is to minimize the amount of plaque and other built-up materials on the artery inner lining to be dislodged and allowed to migrate in the blood stream, an event which could be fatal to the patient in some cases. Again referring to FIG. 16, it can be seen that by rotating the left spiral needle 160 in the clockwise direction, and rotating the right spiral needle 162 in the counterclockwise direction, the graft vessel 152 is penetrated first by the spiral needles, and then the needles pass through the target vessel (usually the coronary artery) from the inside to the outside.

Figure 19:
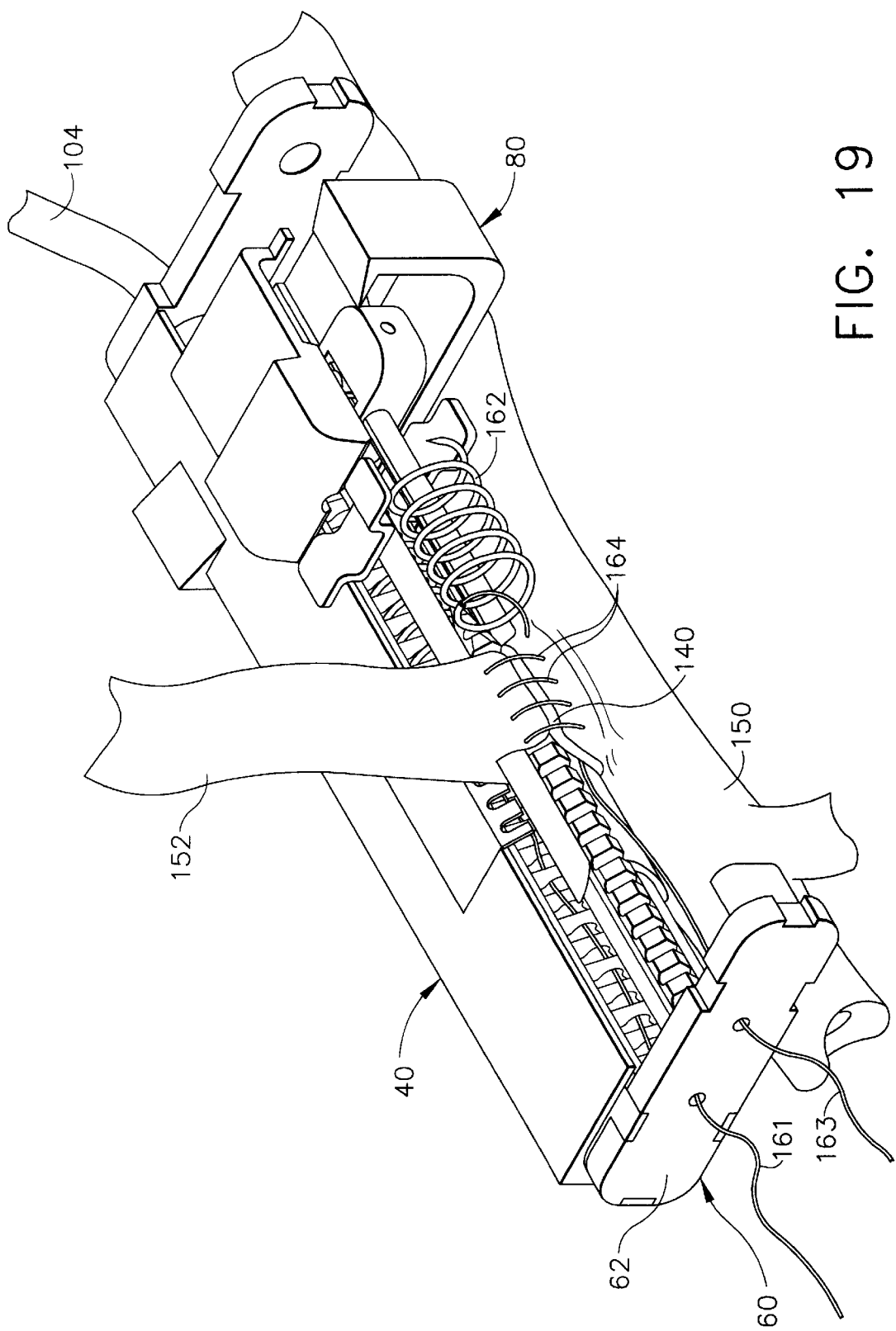
FIG. 19 is an isometric view of the implement, with a part of it removed for clarity, after the suture filaments have been placed into the target and graft blood vessels by the advancement of the spiral needles.

FIG. 19 is a cutaway perspective view of the implement 20 after the spiral needles, 160 and 162, have been fully advanced in the proximal direction. A plurality of stitches, 164, have been placed into the left tissue junction 140 and the right tissue junction 142 (not visible) and the graft and target blood vessels have been joined together. The number of stitches 164 for this embodiment of the implement 20 can vary depending on the initial size of the graft and target blood vessels, 152 and 150. The number and spacing of the stitches can be different from what is shown in FIG. 19, as those skilled in the art can see, by varying the number and spacing of needle guiding features of the implement 20, and by varying the spacing between the windings of the spiral needles, 160 and 162.

Figure 20:
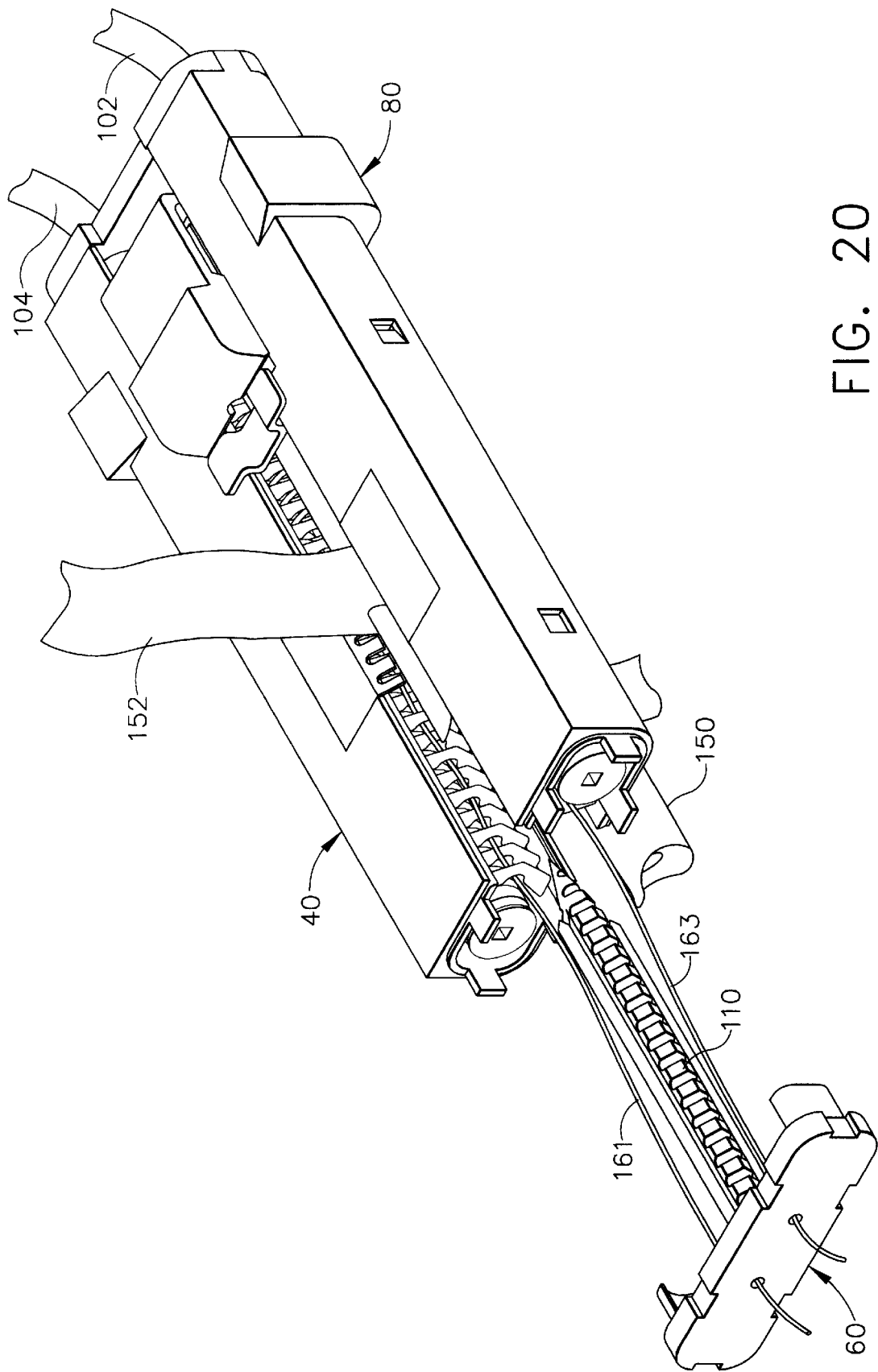
FIG. 20 is a perspective view of the implement of the surgical device depicting the removal of an end cover from the cassette.

FIG. 20 depicts the removal of the end cover 62 and the attached plow 110 from the cassette 60. While this is done, the spiral needles 160 and 162 remain in the positions as shown in FIG. 19. The end cover 62 is next pulled off the ends of the suture filaments 161 and 163 and discarded.

Figure 21:
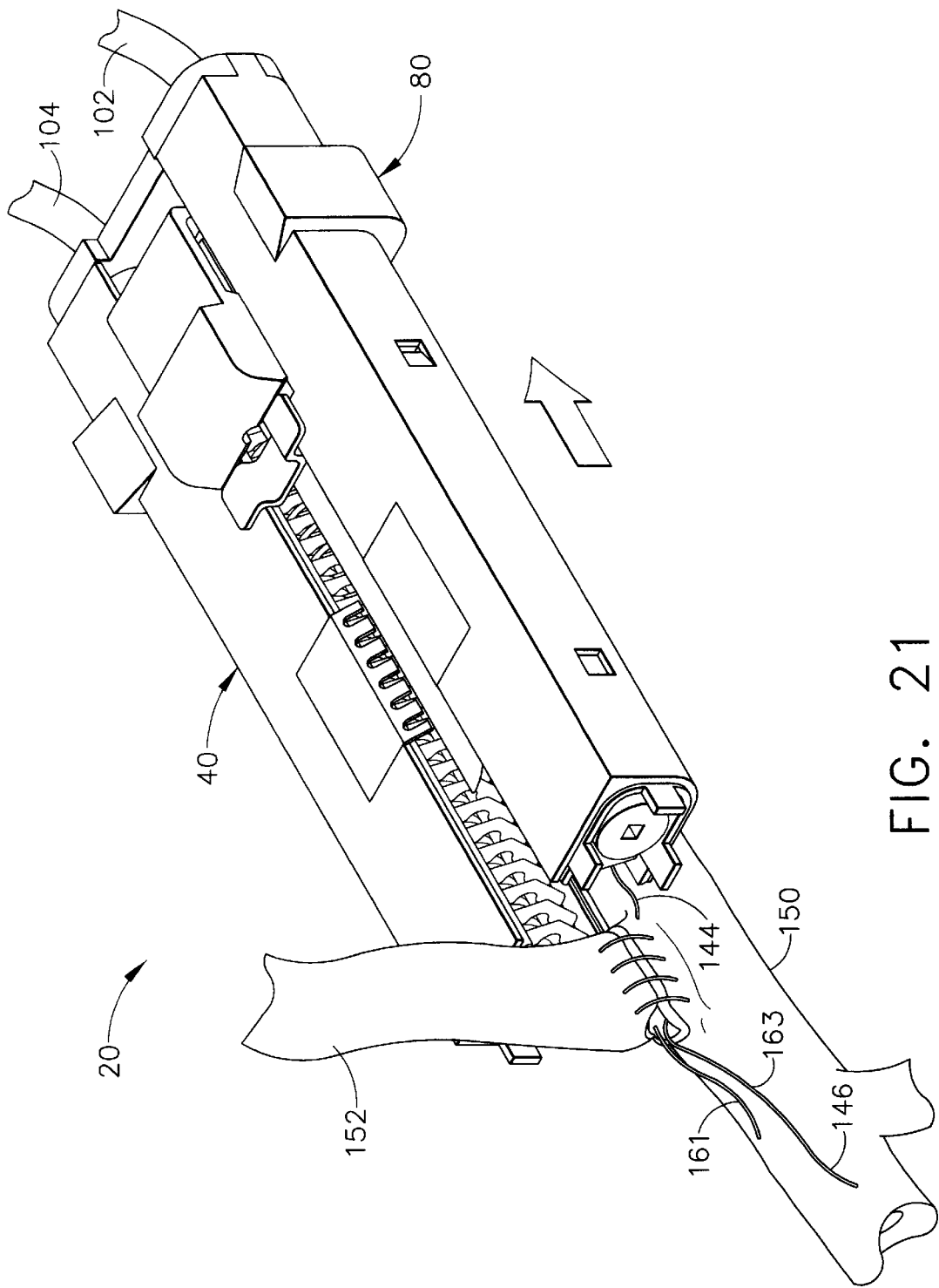
FIG. 21 is an isometric view of the implement depicting the removal of the anastomosed blood vessels from the distal portion.

FIG. 21 shows the removal of the joined blood vessels, 150 and 152, from the implement 20 by gently working the implement off the vessel in the direction shown. Other surgical devices or probes may be used during this step to help free the blood vessels from the implement. As the blood vessels are drawn away from the implement, the suture filaments 161 and 163 are pulled through the tissue junctions 140 and 142 until sufficient lengths of proximal filaments is available for completing the anastomosis.

The anastomosis is completed by severing the proximal filaments 144 near the implement 20, removing the surgical device 10, and tying the two proximal filaments 144 together using a conventional surgeon's knot, and then tying the two distal filaments 146 together, again using a conventional surgeon's knot. The order of tying the knots may be reversed. The excess suture filament can then be trimmed away.

Figure 22:
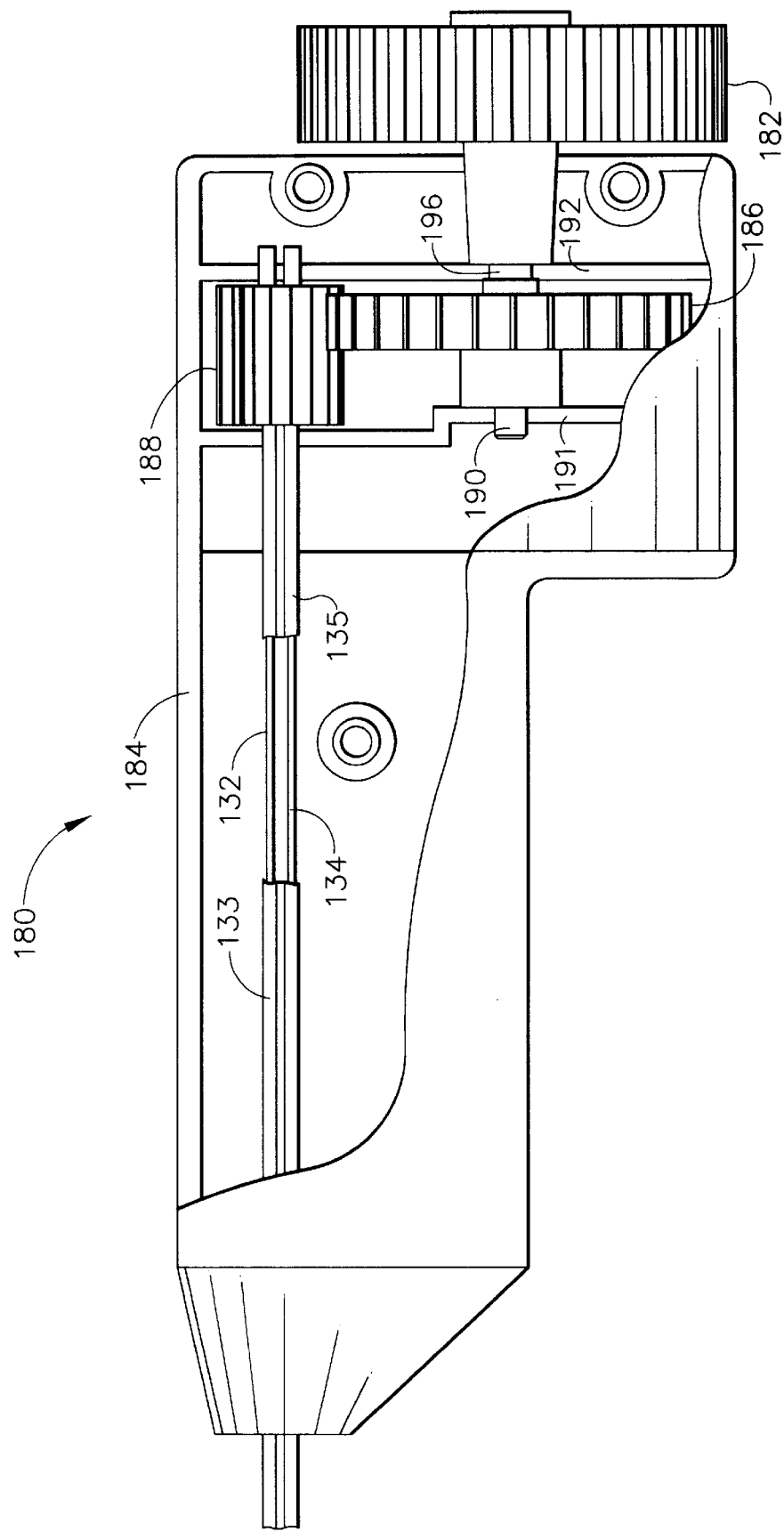
FIG. 22 is a front elevational view of the handle of the surgical device with a portion cutaway to view the internal components.

FIG. 22 is a cut away view of the handle 180 of the surgical device 10 of the present invention. The handle 180 provides the means to actuate the work portion of the cassette 20 in order to advance the spiral needles, 160 and 162, as already described. The handle 180 of this preferred embodiment of the present invention has an elongated, in-line grip with a distal and proximal end. The handle includes a control knob 182 which is mounted in the proximal end and is actuated by rotation in the clockwise direction. The drive section 130 extends from the distal end. The right handle cover 184 is joined to the left handle cover 185 (not shown) by a plurality of fastening pins 197 which press tightly into mating bosses (not shown) on the inside of the left handle cover 185.. Those skilled in the art appreciate that a variety of fastening methods may be used, such as gripper pins, ultrasonically welded joints, screws, and the like.

The two flexible drive members, 104 and 102, of the drive section 130 extend into the handle 180. The right drive member 104 has a flexible wire shaft 132 covered by a sheath 133. The left drive member 102 has a flexible shaft wire 134 covered by a sheath 135. The proximal end of the right drive member 104 is attached to a right pinion gear 188 which is rotatably mounted between handle ribs 191 and 192. Now referring to both FIGS. 22 and 23, right pinion gear rotates about center 189 and meshes with a left pinion gear 193 which is attached to the distal end of left drive member 102 and is rotatably mounted also between handle ribs 191 and 192. Left pinion gear 193 rotates about center 194. The left pinion gear 194 also meshes with drive gear 186. Drive gear 186 is mounted between ribs 191 and 192 and is attached to a control knob boss 196 by a screw 190. Rotation of the control knob 182, therefore, in the clockwise direction causes the drive gear and right pinion gear 188 to rotate in the clockwise direction and the left pinion gear 193 to rotate in the counterclockwise direction. This gearing method provides the oppositely directed rotation of the drive members, 104 and 102.

Figure 23:
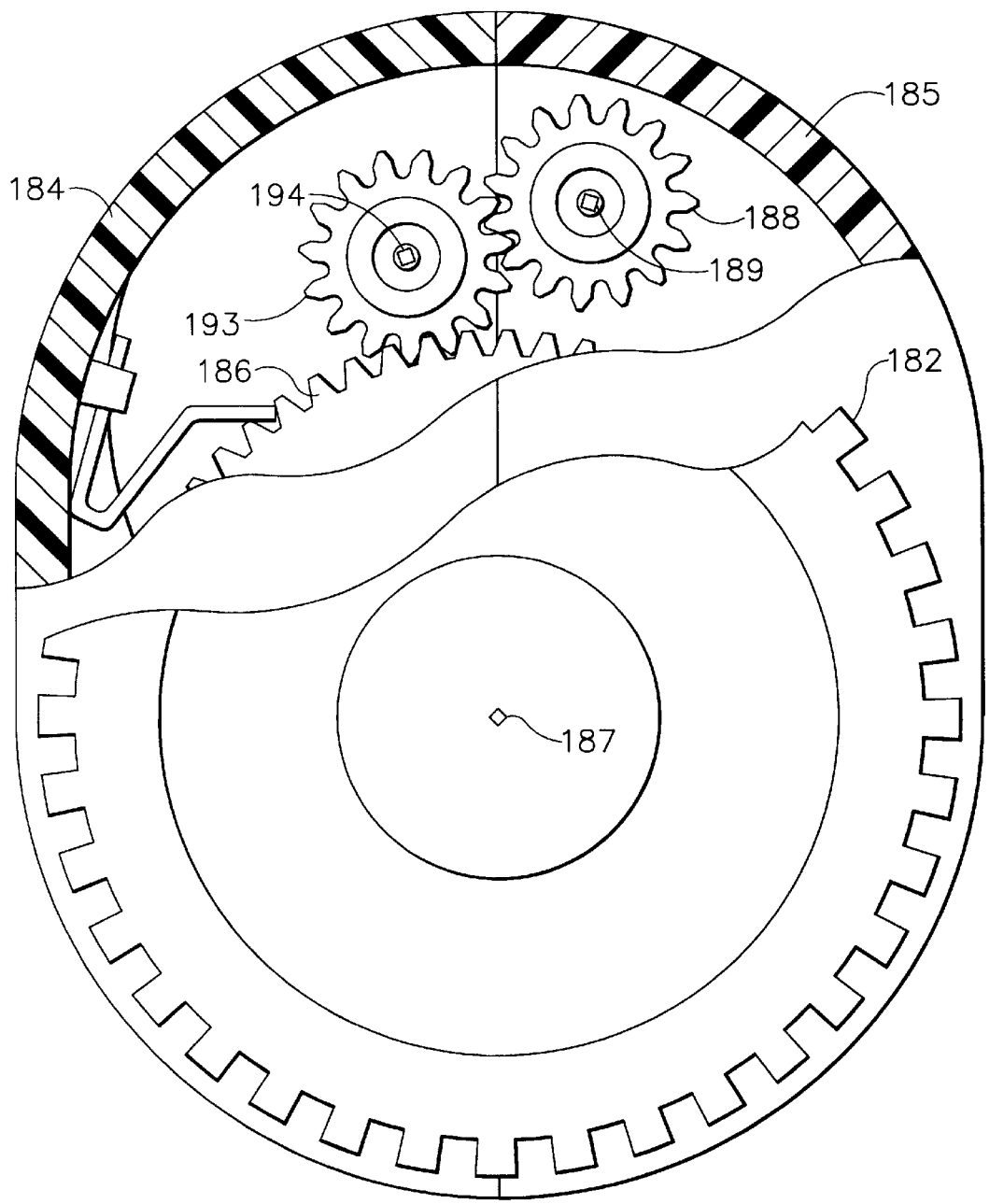
FIG. 23 is a proximal end elevational view of the handle of the surgical device, with a part cutaway to view the internal components.

FIG. 23 shows a proximal end elevational view of the handle, with a portion of the handle covers, 184 and 185, removed to view the internal components. Counterclockwise rotation of the control knob is not desirable in the preferred embodiment of the surgical device 10 because this rotational direction would not serve to advance the spiral needles, 160 and 162, in the proximal direction as required to join the blood vessels with suture filaments. Therefore, the counterclockwise rotation of the control knob is prevented by a one-way pawl spring 198 mounted to the inside of left handle cover 184 and interacting with drive gear 186. However, the surgical device 10 would still be operational without the pawl spring 198. Also, a manual release could also be provided on the handle to allow the surgeon to turn "off and on" the interaction of the pawl spring 198 with the drive gear 186.

Figure 24:
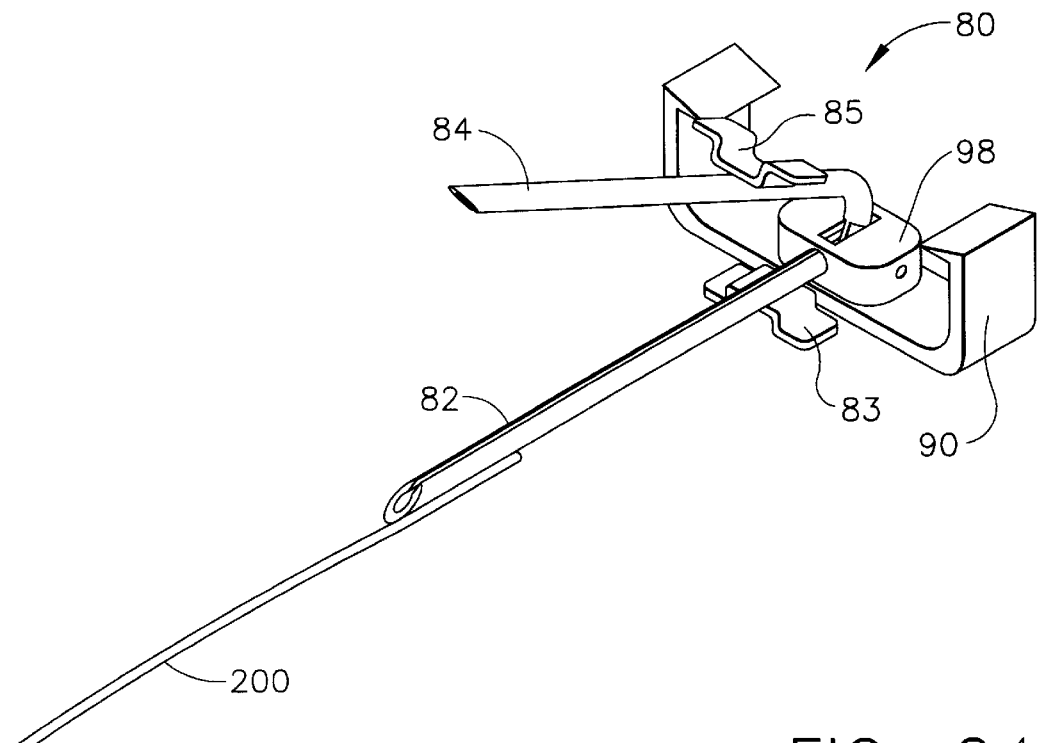
FIG. 24 is an isometric view of an alternate embodiment of the tissue clip shown in FIG. 3.
Figure 25:
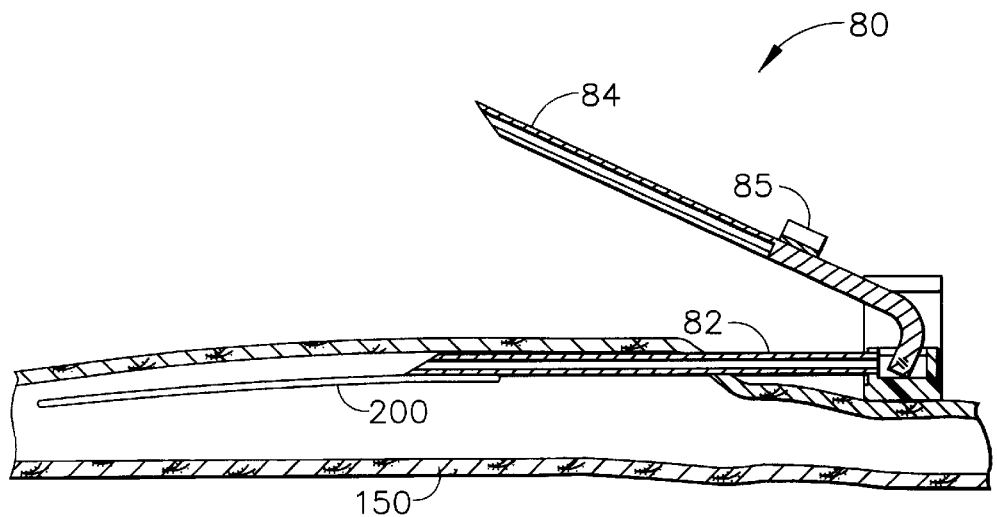
FIG. 25 is a sectional view of the alternate embodiment of the tissue clip inside a target blood vessel such as the coronary artery.

Turning now to FIG. 24, an alternate embodiment of the tissue clip 80 shown in FIG. 3 is depicted. In FIG. 24, a flexible tip 200 is shown attached to the first prong 82. The flexible tip 82 is an elongated filament which may be solid or tubular, and is made of a flexible, biocompatible polymer such as polyethylene. It is attached to the first prong 82 using preferably a biocompatible adhesive, although mechanical and other methods of attachment are well-known to those skilled in the art. The flexible tip 200 serves as a means for facilitating the introduction of the first prong into an aperture of a hollow organ, by providing a steerable and atraumatic extension to the rigid first prong 82. A similar flexible tip may also be provided on the second prong 84. In FIG. 25, the first prong 82 of the alternate embodiment of tissue clip 80 is shown inserted into a target blood vessel 150, such as a coronary artery. In this view, it can be seen how the first prong 82 enters but does not exit the target blood vessel 150. This usage differs from how the first embodiment of the tissue clip 80 is used as shown in FIG. 6, in which the first prong 82 both enters and exits the blood vessel 150. The second embodiment of the tissue clip 80 requires the creation with a surgical scalpel of an aperture in the wall of the target blood vessel 150, prior to insertion of the flexible tip 200. For the first embodiment shown in FIG. 6, creation of an aperture is not necessary. Even with the addition of an additional step when using the second embodiment, the insertion of the first prong into the blood vessel cases be cases be easier for the surgeon than when using the first embodiment without the flexible tip 200. Usage of the present invention with the flexible tip 200 is otherwise identical to that which has already been described.

While a preferred embodiment of the present invention has been shown and described herein, it will be obvious to those skilled in the art that such an embodiment is provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical device for attaching a first hollow organ to a second hollow organ and creating a passageway therebetween, said surgical device comprising:

a) a first means for holding said first hollow organ, and a second means for holding said second hollow organ, said first and second means having proximal ends attached to said surgical device, distal ends extending therefrom and longitudinal axis extending therebetween, said surgical device including means for moving at least one of said first and second means adjacent to the other so as to move said hollow organs close together;

b) a plow having a proximal end, a distal end extending therefrom and a longitudinal axis extending therebetween, said plow for incising at least one of said hollow organs so as to create a passageway between said hollow organs; and c) a frame for coupling said first and second means and said plow together in operational engagement, said surgical device further including a means for driving a needle, having a suture attached thereto, through said organs, about said passageway thereby attaching said hollow organs together.

2. The device according to claim 1 wherein said first and second means for holding said hollow organs comprise prongs.

3. The device according to claim 1 wherein said first and second means for holding said hollow organs comprise clamps.

4. A surgical device for attaching a first hollow organ to a second hollow organ and creating a passageway therebetween, said surgical device comprising:

a) a first member comprising a first prong for entering a wall of said first hollow organ, and a second prong for entering a wall of said second hollow organ, said prongs having proximal ends attached to said first member, distal ends extending therefrom and longitudinal axis extending therebetween, said surgical device including a means for moving said distal ends of said prongs adjacent to one another so as to move said hollow organs close together;

b) a second member comprising a plow, said plow having a proximal end attached to said second member, a distal end extending therefrom and a longitudinal axis extending therebewteen, said distal end of said plow is able to incise at least one of said hollow organs so as to create a passageway between said hollow organs; and c) a frame for coupling said first and second members together in operational engagement, said surgical device further including a means for driving a needle, having a suture attached thereto, so as to drive said needle through said organs, about said passageway thereby attaching said hollow organs together.

5. The surgical device of claim 4 wherein said second member further comprises two sets of needle paths extending substantially parallel to said longitudinal axis of said plow with said plow disposed therebetween, said needle paths guide said needle along said paths so as to attach said organs together.

6. The surgical device of claim 5 further including two spiral needles, each having a suture attached thereto, engaged with said driver, said spiral needles passing through said needle paths and through said walls of said hollow organs.

7. The device according to claim 6, wherein said needle paths comprise a plurality of grooves on said second member, spaced apart from said plow.

8. The device according to claim 6, wherein said needle paths comprise a plurality of grooves on either side of said plow extending along its longitudinal axis.

9. The surgical device of claim 4 further comprising a means for removal of said first and second hollow organs from said surgical device after said passageway has been created and said sutures have been placed so as to join said hollow organs together.

10. The surgical device of claim 4 wherein at least one of said first prong and said second prong has a distal, flexible tip attached thereto.

11. The device according to claim 4 wherein said means for moving said distal ends of said prongs adjacent to one another so as to move said hollow organs close together comprises at least one of said proximal ends of said prongs being attached to said first member by a pivotable connection.

12. A surgical device for attaching a first hollow organ to a second hollow organ and creating a passageway therebetween, said surgical device comprising:

a) a tissue clip comprising a first prong for entering a wall of said first hollow organ and a second prong for entering a wall of said second hollow organ, said prongs having proximal ends attached to said tissue clip, distal ends extending therefrom and longitudinal axis therebetween, at least one of said prongs being pivotable at its proximal end so that said hollow organs can be moved close together;

b) a cassette comprising a plow, said plow having a proximal end attached to said cassette, a distal end extending therefrom and a longitudinal axis extending therebewteen, said distal end of said plow is able to incise at least one of said hollow organs so as to create a passageway between said hollow organs; and c) a frame for coupling said tissue clip and cassette together in operational engagement, said surgical device further including a driver for driving a needle, having a suture attached thereto, through said organs, about said passageway, thereby attaching said hollow organs together.

13. The surgical device of claim 12 wherein said cassette further comprises two sets of needle paths extending substantially parallel to said longitudinal axis of said plow with said plow disposed therebetween, said needle paths guide said needle along said paths so as to attach said organs together.

14. The surgical device of claim 13 further including two spiral needles, each having a suture attached thereto, engaged with said driver, said spiral needles passing through said needle paths and through said walls of said hollow organs.

15. The surgical device according to claim 12, wherein said frame couples said cassette and tissue clip in operational engagement such that said longitudinal axis of said prongs and said plow are substantially parallel.

16. The device according to claim 14, wherein said needle paths comprise a plurality of grooves on said cassette, spaced apart from said plow.

17. The device according to claim 14, wherein said needle paths comprise a plurality of grooves on either side of said plow extending along its longitudinal axis.

18. The surgical device of claim 12 further comprising a means for removal of said first and second hollow organs from said surgical device after said passageway has been created and said sutures have been placed so as to join said hollow organs together.

19. The surgical device of claim 12 wherein at least one of said first prong and said second prong has a distal, flexible tip attached thereto.

20. A surgical device for attaching a first hollow organ to a second hollow organ and creating a passageway therebetween, said surgical device comprising:

a) a handle attached to a proximal end of said surgical device for holding said surgical device, and a frame attached to a distal end of said surgical device for coupling a tissue clip and a cassette together in operational engagement;

b) said tissue clip comprising a first prong for entering a wall of said first hollow organ and a second prong for entering a wall of said second hollow organ, said prongs having proximal ends attached to said tissue clip, distal ends extending therefrom and longitudinal axis therebetween, at least one of said prongs being pivotable at its proximal end so that said hollow organs can be moved close together;

c) said cassette comprising a plow, said plow having a proximal end attached to said cassette, a distal end extending therefrom and a longitudinal axis extending therebewteen, said distal end of said plow is able to incise at least one of said hollow organs so as to create a passageway between said hollow organs, said cassette further comprises two sets of needle paths extending substantially parallel to said longitudinal axis of said plow with said plow disposed therebetween; and d) a driver for driving a pair of spiral needles, having a suture attached thereto, through said organs, about said passageway, thereby attaching said hollow organs together, said needle paths guide said needles along said paths so as to attach said organs together.

21. The surgical device according to claim 20, wherein said frame couples said cassette and tissue clip in operational engagement such that said longitudinal axis of said prongs and said plow are substantially parallel.

22. The device according to claim 20, wherein said needle paths comprise a plurality of grooves on said cassette, spaced apart from said plow.

23. The device according to claim 20, wherein said needle paths comprise a plurality of grooves on either side of said plow extending along its longitudinal axis.

24. The surgical device of claim 20 further comprising a means for removal of said first and second hollow organs from said surgical device after said passageway has been created and said sutures have been placed so as to join said hollow organs together.

25. The surgical device of claim 20 wherein at least one of said first prong and said second prong has a distal, flexible tip attached thereto.

* * * * *